United States Patent [19]
Erickson et al.

[11] Patent Number: 5,441,527
[45] Date of Patent: Aug. 15, 1995

[54] IMPLANTABLE BONE GROWTH STIMULATOR AND METHOD OF OPERATION

[75] Inventors: John H. Erickson, Plano; John C. Tepper, Carrollton; Ike C. Thacker, Dallas, all of Tex.; Gregg Turi, Wood-Ridge, N.J.; Anthony J. Varrichio, Flanders, N.J.; Arthur A. Pilla, Ridgewood, N.J.

[73] Assignee: AMEI Technologies Inc., Wilmington, Del.

[21] Appl. No.: 186,230

[22] Filed: Jan. 24, 1994

Related U.S. Application Data

[63] Continuation of Ser. No. 839,199, Feb. 20, 1992, abandoned.

[51] Int. Cl.⁶ .............................................. A61N 1/32
[52] U.S. Cl. .................................... 607/51; 607/116; 607/117; 607/70; 607/74
[58] Field of Search .................... 607/50, 52, 115, 116, 607/117, 70, 72, 76, 9, 74

[56] References Cited

U.S. PATENT DOCUMENTS

| | | | |
|---|---|---|---|
| D. 320,659 | 10/1961 | Johansson et al. | |
| D. 353,889 | 12/1994 | Erickson et al. | D24/155 |
| 2,067,589 | 1/1937 | Antrim | |
| 2,298,232 | 10/1942 | Remund | |
| 3,055,372 | 9/1962 | Browner | 128/421 |
| 3,702,755 | 11/1972 | Palmer | |
| 3,745,995 | 7/1973 | Kraus | |
| 3,783,880 | 1/1974 | Kraus | |
| 3,842,841 | 10/1974 | Brighton et al. | 128/419 F |
| 3,874,372 | 4/1975 | LeBon | |
| 3,881,873 | 5/1975 | Klowden | |
| 3,890,953 | 6/1975 | Kraus et al. | |
| 3,892,552 | 7/1975 | Gay, Jr. | |
| 3,914,900 | 10/1975 | Bigelow et al. | |
| 3,915,151 | 10/1975 | Kraus | 128/419 F |
| 3,918,440 | 11/1975 | Kraus | 128/419 FX |
| 3,946,762 | 3/1976 | Green | |
| 4,026,304 | 5/1977 | Levy | 128/419 F |
| 4,105,017 | 8/1978 | Ryaby et al. | 600/14 |
| 4,216,548 | 8/1980 | Kraus | 3/1.91 |
| 4,232,679 | 11/1980 | Schulman | |
| 4,237,895 | 12/1980 | Johnson | 128/419 PG |
| 4,313,438 | 2/1982 | Greatbatch | 128/419 F |
| 4,314,554 | 2/1982 | Greatbatch | 128/419 F X |
| 4,333,469 | 6/1982 | Jeffcoat et al. | 128/419 F |
| 4,344,250 | 8/1982 | Fahlstrom | |
| 4,414,979 | 11/1983 | Hirshorn et al. | 128/419 F |

(List continued on next page.)

FOREIGN PATENT DOCUMENTS

| | | |
|---|---|---|
| 0305791 | 3/1989 | European Pat. Off. |
| 0561068 | 9/1993 | European Pat. Off. |
| 1466730 | 6/1987 | U.S.S.R. |
| 8302901 | 9/1983 | WIPO |

OTHER PUBLICATIONS

Zimmer USA, "The Alternate Treatment of Fracture Nonunion—Electrical Stimulation to Induce Osteogenesis" Brochure Sep. 1979.

A. Paul Brokaw, "A Simple Three-Terminal IC Bandgap Reference", *IEEE Journal of Solid-State Circuits*, Dec. 1974, pp. 388–393.

Saba, Joseph M., "Echo-Encephalography", *Medical Electronics*, Sep.–Oct. 1970, pp. 96–103.

Dohrmann, George J. and Rubin, Jonathan M., "Intraoperative Ultrasound Imaging of the Spinal cord: Syringomyelia, Cysts, and Tumors—A Preliminary Report", *Surgical Neurologist*, vol. 18, No. 6, Dec. 1982, pp. 395–399, Little, Brown, & Co., Boston, Mass.

*Primary Examiner*—Lee S. Cohen
*Assistant Examiner*—Jeffrey R. Jastrzab
*Attorney, Agent, or Firm*—Baker & Botts

[57] ABSTRACT

A method for the therapeutic stimulation of bone growth of a bone site is disclosed comprising the steps of implanting first and second electrodes into the tissue near the base site. The electrodes are coupled to a bone growth stimulator which generates an alternating current.

22 Claims, 14 Drawing Sheets

U.S. PATENT DOCUMENTS

| | | | |
|---|---|---|---|
| 4,432,361 | 2/1984 | Christensen et al. | 128/419 F |
| 4,459,988 | 7/1984 | Dugot | 128/419 F |
| 4,461,300 | 7/1984 | Christensen | 128/419 F |
| 4,467,808 | 8/1984 | Brigton et al. | 128/419 F |
| 4,506,673 | 3/1985 | Bonnell | 128/419 F |
| 4,506,674 | 3/1985 | Brighton et al. | 128/419 F |
| 4,514,865 | 5/1985 | Harris . | |
| 4,519,394 | 5/1985 | Black et al. | 128/419 F |
| 4,530,360 | 7/1985 | Durante . | |
| 4,535,775 | 8/1985 | Brighton et al. . | |
| 4,549,546 | 10/1985 | Kelly et al. | 128/419 F |
| 4,549,547 | 10/1985 | Brighton et al. | 128/419 F |
| 4,550,370 | 10/1985 | Baker . | |
| 4,556,051 | 12/1985 | Maurer . | |
| 4,561,426 | 12/1985 | Stewart . | |
| 4,561,443 | 12/1985 | Hogrefe et al. . | |
| 4,598,713 | 7/1986 | Hanjurgens et al. . | |
| 4,600,010 | 7/1986 | Dugot . | |
| 4,602,638 | 7/1986 | Adams | 128/419 F |
| 4,611,597 | 9/1986 | Kraus | 128/419 F |
| 4,613,937 | 9/1986 | Batty, Jr. . | |
| 4,619,264 | 10/1986 | Singh | 128/419 F |
| 4,651,468 | 3/1987 | Martinez . | |
| 4,654,574 | 3/1987 | Thaler | 320/14 |
| 4,665,896 | 5/1987 | LaForge et al. . | |
| 4,665,920 | 5/1987 | Campbell | 128/422 |
| 4,679,560 | 7/1987 | Galbraith . | |
| 4,683,896 | 8/1987 | Herbst et al. | 128/785 |
| 4,781,591 | 11/1988 | Allen | 433/174 |
| 4,785,244 | 11/1988 | Jin et al. | 324/260 |
| 4,793,325 | 12/1988 | Cadossi et al. . | |
| 4,889,111 | 12/1989 | Ben-Dov | 128/419 F |
| 4,905,671 | 3/1990 | Senge et al. . | |
| 4,944,299 | 7/1990 | Silivan . | |
| 4,974,114 | 11/1990 | Kammerer . | |
| 4,993,413 | 2/1991 | McLeod et al. | 128/419 F |
| 5,000,178 | 3/1991 | Griffith | 128/419 F |
| 5,014,699 | 5/1991 | Pollack et al. | 128/419 F |
| 5,030,236 | 7/1991 | Dean . | |
| 5,038,780 | 8/1991 | Boetzkes . | |
| 5,056,518 | 10/1991 | Pethica et al. . | |
| 5,058,582 | 10/1991 | Thaler | 128/419 R |
| 5,088,488 | 2/1992 | Markowitz et al. . | |
| 5,103,806 | 4/1992 | McLeod et al. . | |
| 5,154,172 | 10/1992 | Terry, Jr. et al. . | |
| 5,191,880 | 3/1993 | McLeod et al. . | |

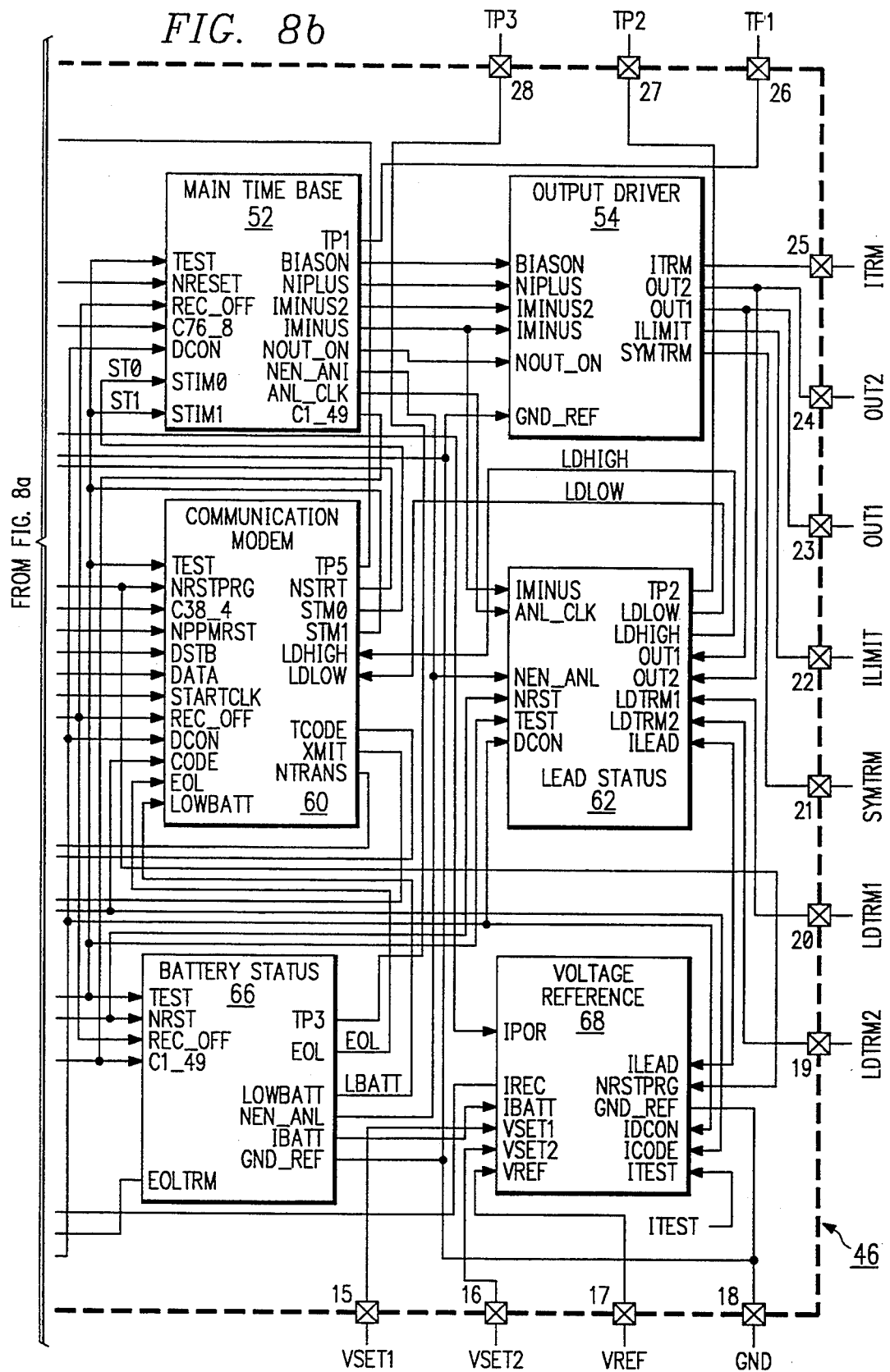

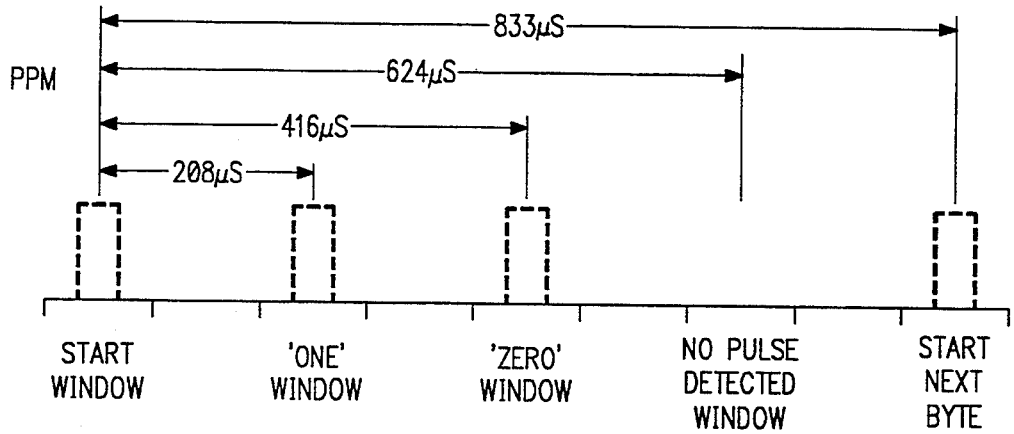

FIG. 9a

DOWN-LINK

| START | RNW | STIM0 | STIM1 | 'ZERO' | 'ONE' | 'ONE' | 'ZERO' | DCON | CODE | STOP |
|---|---|---|---|---|---|---|---|---|---|---|
| 1 | 0=WRITE<br>1=READ | 0  OFF  0<br>1  4 HOURS  0<br>0  8 HOURS  1<br>1  CONTIN.  1 | | 0 | 1 | 1 | 0 | MUST FOLLOW<br>HARD WIRED<br>CONTROL BITS | | 0 |

FIG. 9b

UP-LINK

| START | STIM0 | STIM1 | DCON | CODE | LEAD0 | LEAD1 | BATT0 | BATT1 | PARITY | STOP |
|---|---|---|---|---|---|---|---|---|---|---|
| 1 | 0  OFF  0<br>1  4 HOURS  0<br>0  8 HOURS  1<br>1  CONTIN.  1 | | WILL FOLLOW<br>HARD WIRED<br>CONTROL BITS | | 0  LEAD OK  0<br>1  LEAD LOW  0<br>0  LEAD HI  1<br>1  N/A  1<br>DC MODE<br>0  LEADS OK  0<br>1  LD1 HIGH  0<br>0  LD2 HIGH  1<br>1  BOTH HIGH  1 | | 0  BATT OK  0<br>1  LOW BATT  0<br>0  N/A  1<br>1  EOL  1 | | ODD<br>PARITY | 0 |

FIG. 9c

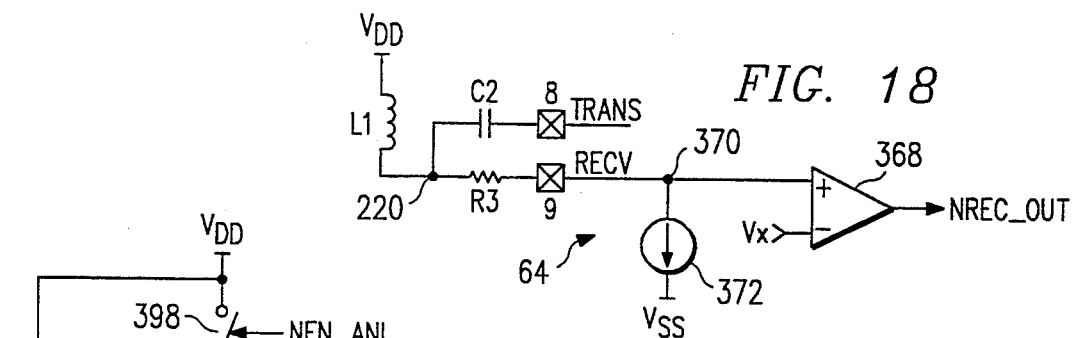
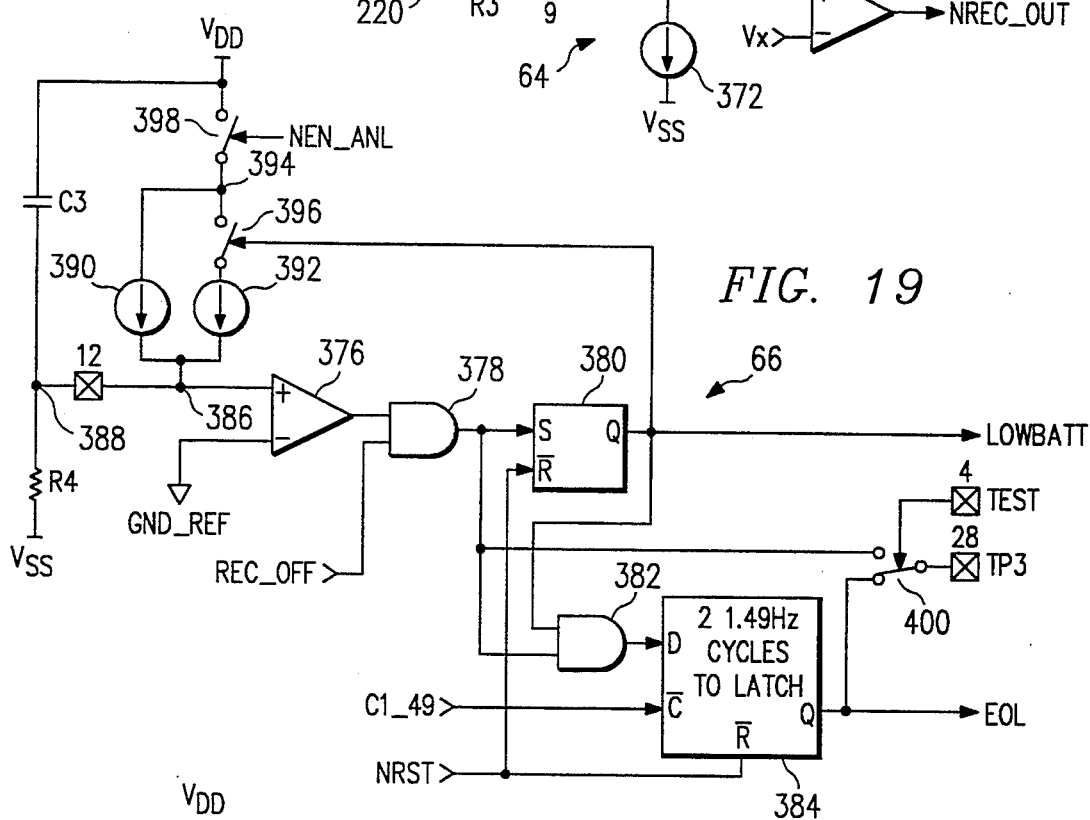
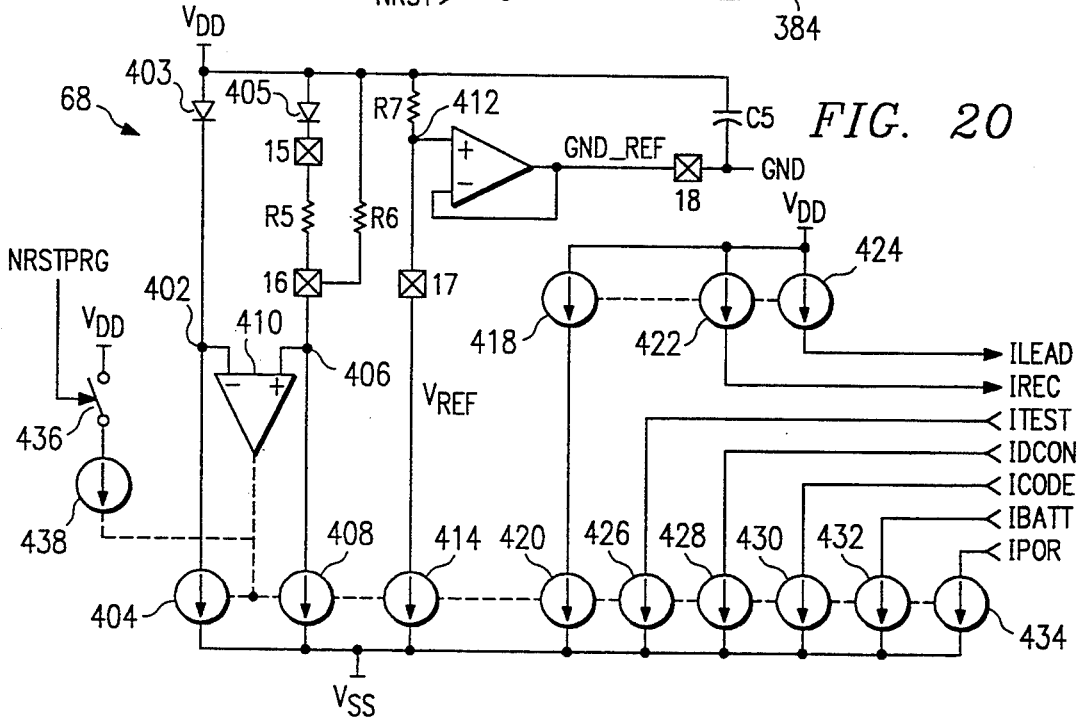

IMPLANTABLE BONE GROWTH STIMULATOR AND METHOD OF OPERATION

CROSS-REFERENCE TO RELATED APPLICATIONS

This application is a continuation of application Ser. No. 07/839,199 filed Feb. 20, 1992, entitled "IMPLANTABLE BONE GROWTH STIMULATOR AND METHOD OF OPERATION", now abandoned. This application is also related to U.S. application Ser. No. 08/018,944 filed Feb. 17, 1993, entitled "IMPLANTABLE TISSUE GROWTH STIMULATOR AND METHOD OF OPERATION", U.S. application Ser. No. 08/239,401, filed May 5, 1994, entitled "APPARATUS AND METHOD FOR STIMULATING TISSUE GROWTH WITH ULTRASOUND", U.S. Design application Ser. No. 29/004,938, filed Feb. 17, 1993, entitled "HAND-HELD PROGRAMMER/MONITOR", and U.S. Design application Ser. No. 29/004,975 filed Feb. 17, 1993, entitled "IMPLANTABLE GROWTH STIMULATOR" now U.S. Des. Pat. No. D353,889.

TECHNICAL FIELD OF THE INVENTION

This invention relates in general to medical devices, and more particularly to an implantable bone growth stimulator and method of operation.

BACKGROUND OF THE INVENTION

Known bone growth stimulators generally fall into at least two broad categories. The first category consists of implantable direct current ("DC") devices. The generator of such stimulators are implanted in the body near the site of a bone fracture or a fusion. A cathode typically exits the case of the DC stimulator leading directly to the bone injury site. The stimulator case acts as the anode. Electronics within the stimulator cause a direct current to flow between cathode and anode and thereby through the bone fracture or fusion site generally. A second class of bone growth stimulators are external or noninvasive stimulators. These stimulators are aligned adjacent to a bone fracture or fusion site outside the body. Typically, these devices generate either a pulsed electromagnetic field ("PEMF") or a 60 kHz sinusoidal electric field to promote healing at the bone injury site. These subgroups of noninvasive stimulators are referred to as PEMF and capacitive coupling stimulators.

There are numerous disadvantages associated with known direct current implantable bone growth stimulators. In general, the DC characteristics of these stimulators require the leads to be routed directly to the bone injury site. It is believed that the chemical change at the cathode surface induces bone growth. Additionally, the cathode (or cathodes) is usually embedded in the fracture or bone graft mass. It may be required during explant of the stimulator that the implanted cathode be left in the body. This may be necessary after the bone heals and encapsulates the cathode originally implanted into the bone mass. If the cathode is damaged, or otherwise becomes inoperative, extensive surgery will be required to replace it at the bone site. This increases the likelihood of surgical complications such as infection. Also, the DC stimulator and its cathode will degrade imaging results due to their proximity to relevant body structures. Imaging techniques such as magnetic resonance imaging, computer-aided tomography and x-ray photography will all be affected.

External bone growth stimulators also have disadvantages associated with them. Because of their placement outside the human body, these stimulators are vulnerable from ambulatory or semiambulatory patients. Their movement, whether intentional or inadvertent, may cause damage to the unit. These devices are also cumbersome and usually require the patient to operate them. This creates a question of patient compliance and ultimately of stimulator effectiveness. Furthermore, capacitive coupled stimulators require a conductive gel between the patient's skin and each electrode. This gel must be replaced often and is known to cause skin irritation.

Most known stimulators simply are turned on by the manufacturer and turned off when the stimulator battery dies or the power supply is otherwise disconnected. U.S. Pat. No. 4,414,979 to Hirshorn, entitled "Monitorable Bone Growth Stimulator" issued Nov. 15, 1983, discloses an implantable DC bone growth stimulator which transmits pulses of electromagnetic energy at a rate proportional to the current being delivered to the injury site. This allows some degree of monitorability of the energy delivered to the bone site. However, other parameters of bone growth stimulators are also of interest. It may be important for the attending physician to know the mode of operation of the stimulator, the expected lifetime of the associated stimulator battery, and the condition of the leads. Conversely, it is also desirable to be able to program certain operating modes of a bone growth stimulator. Such capability is particularly important with implantable bone growth stimulators since they are inaccessible otherwise. Such monitorability and programmability have not been available with prior implantable stimulators.

Therefore, a need has arisen for a bone growth stimulator which is implantable, which is easily replaced and completely removable after use, which is both monitorable and programmable during operation, which does not require patient participation, and which does not interfere with imaging results.

SUMMARY OF THE INVENTION

In accordance with the present invention, an implantable bone growth stimulator is provided which substantially eliminates or reduces disadvantages and problems associated with prior bone growth stimulators.

A method for the therapeutic stimulation of bone repair of a bone site is disclosed comprising the steps of implanting first and second electrodes into the tissue near the bone site. The electrodes are coupled to a bone growth stimulator which generates an alternating current.

The first technical advantage of the device is its implantability. The unit is completely self-contained and is suitable for implantation in the human body. The implantability of the stimulator reduces the vulnerability of the device to accidental injury and renders moot the issue of patient compliance. This increases both the reliability and effectiveness of the stimulator.

A second technical advantage of the invention is its AC nature. Because the device is AC, the electrodes may be placed away from the injury site, e.g. subcutaneously. This causes less trauma to the surrounding tissue during implant and explant, reduces the chances of infection and increases imaging results. Further, the remote placement requires no change in conventional orthopedic surgical procedures.

A third technical advantage of the device is its programmability. The operation of the device may be modified by an external transmitter/receiver during its lifetime to better suit the needs of the patient. A magnetic pulse is used to relay digital signals to the stimulator.

A fourth technical advantage of the device is its monitorability. The device has the ability to monitor important characteristics of its operation and report these via a low frequency magnetic pulse to an external device for an evaluation by a physician. This insures maximum therapeutic value to the patient. The patient can avoid wearing a defective bone growth stimulator if such defect can be determined and remedied.

The final technical advantage of the device is the disclosed electrode structure. The electrodes are two flat conductive surfaces located on one face of the disclosed stimulator. A physician may implant the device such that the electrodes face away from the underlying bone structure and surrounding muscle mass. This has been shown to increase the effectiveness of the stimulator.

BRIEF DESCRIPTION OF THE DRAWINGS

For a more complete understanding of the present inventions and the advantages thereof, reference is now made to the following descriptions taken in conjunction with the accompanying drawings, in which:

FIGS. 8a and 8b depict left and right halves of a block diagram of the application specific integrated circuit used in the bone growth stimulator depicted in FIGS. 1 through 3;

FIG. 9a is a graphical representation of the communication protocol used by the circuit depicted in FIGS. 8a and 8b;

FIGS. 9b and 9c depict tables containing an explanation of the down-link program data word and up-link handshake, respectively, of the circuit depicted in FIGS. 8a and 8b;

FIG. 10 illustrates a block diagram of the crystal oscillator circuit depicted in FIG. 8a;

FIG. 11 illustrates a block diagram of the power on reset circuit depicted in FIG. 8a;

FIG. 14 illustrates schematically the transmitter circuit depicted in FIG. 8a;

FIGS. 15a and 15b illustrate schematically the PPM decoder circuit depicted in FIG. 8a;

FIG. 18 illustrates schematically the receiver circuit depicted in FIG. 8a;

FIG. 19 illustrates schematically the battery status indicator circuit depicted in FIG. 8b;

FIG. 20 illustrates a block diagram of the voltage reference/regulator circuit depicted in FIG. 8b;

DETAILED DESCRIPTION OF THE INVENTION

The preferred embodiment of the present invention and its advantages are best understood by referring to FIGS. 1 through 22 of the drawings, like numerals being used for like and corresponding parts of the various drawings.

The present invention will be described in conjunction with the following Table of Contents:

A. MECHANICAL PACKAGING
  1. AC Configuration
  2. DC Configuration
B. OUTPUT CHARACTERISTICS
  1. AC Configuration
  2. DC Configuration
C. IMPLANTATION CONFIGURATION
  1. AC Configuration
  2. DC Configuration
D. ELECTRONIC IMPLEMENTATION
  1. Overview
  2. Communications Protocol
  3. Signal/External Input Description
  4. Circuit Description
    a. Crystal Oscillator
    b. Power-On Reset
    c. Main Time Base
    d. Output Driver
    e. Transmitter
    f. PPM Decoder
    g. Communications Modem
    h. Lead Status
    i. Receiver
    j. Battery Status Indicator
    k. Voltage Reference/Regulator
  5. Stimulator Circuit Configurations
    a. AC Configuration
    b. DC Configuration

A. MECHANICAL PACKAGING

1. AC Configuration

Figure 1:
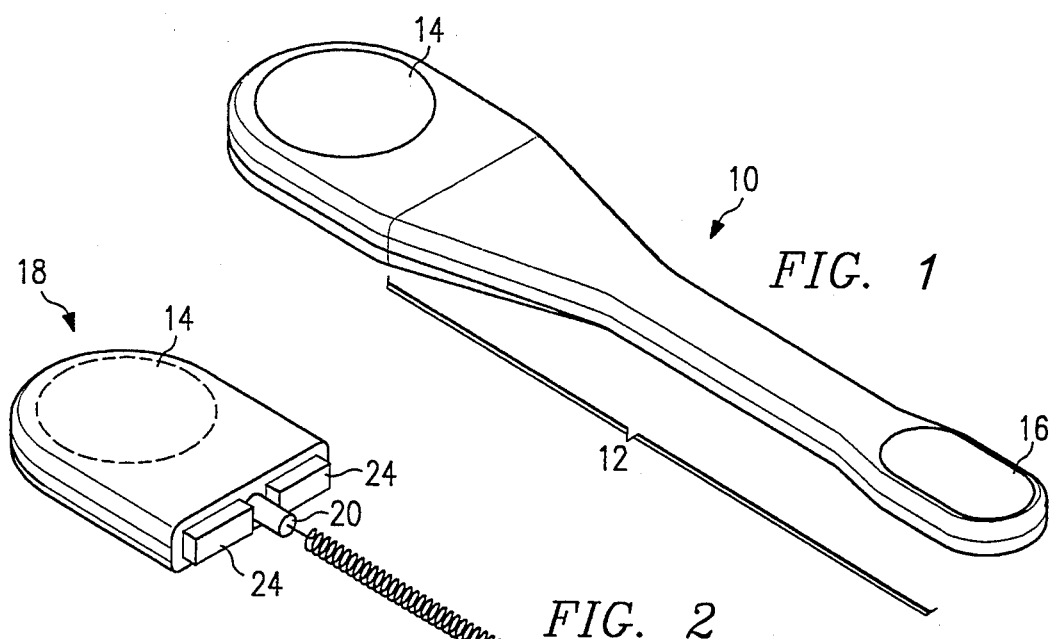
FIGS. 1 and 2 are isometric illustrations of the disclosed bone growth stimulator configured for generating an alternating current output.
Figure 2:
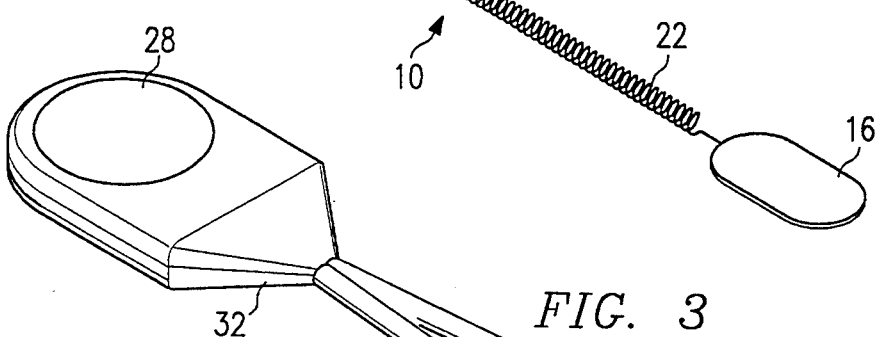

FIGS. 1 and 2 are isometric illustrations of the disclosed bone growth stimulator configured for generating an alternating current output. In particular, FIG. 1 depicts the AC bone growth stimulator ready for implantation into a patient. FIG. 2 depicts the disclosed bone growth stimulator prior to final assembly.

FIG. 1 depicts a bone growth stimulator configured for an alternating current ("AC") output generally at 10. (Hereinafter the "AC stimulator"). AC stimulator 10 comprises a thin elongate arm 12 made of a flexible elastomeric material connecting a first electrode 14 and a second electrode 16. Arm 12 maintains a predetermined distance between electrodes 14 and 16 while AC stimulator 10 is generally flat. Arm 12, however, flexes allowing AC stimulator 10 to more readily conform to the contours of the patient into which it is surgically implanted.

In the preferred embodiment, arm 12 is fabricated from silicon manufactured by Dow-Corning designated MDX 4-4516. Other implantable grade materials such as urethane and silicon-urethane blends may be used in place of silicon. Electrodes 14 and 16 are manufactured from titanium. Additionally, electrode 14 is an exposed portion of a titanium housing imbedded in AC stimulator 10. (shown in FIG. 2.) The housing is coated with an electrically non-conductive material such as parylene such that no portion of titanium other than electrode 14 is exposed. AC stimulator 10 is approximately 6 inches long and 0.2 inches thick. Approximately 5.5 inches of AC stimulator 10 consists of arm 12. The remaining portion of AC stimulator 10 comprises a coated electronics housing (shown in FIG. 2).

In operation, AC stimulator 10 generates an alternating current between electrodes 14 and 16. The resulting electric field may be used to stimulate bone healing.

FIG. 2 depicts AC stimulator 10 before arm 12 has been formed and before a non-conducting layer of parylene has been applied to a housing 18. Housing 18 comprises a feed-through assembly 20. Feed-through assembly 20 passes an electrical lead 22 to electrode 16. The dashed line on housing 18 indicates the location of electrode 14 after final assembly. Additionally, housing 18 has two lips 24 which have an irregular surface. Lips 24 thereby facilitate a secure union between arm 12 (shown in FIG. 1) and housing 18.

In one embodiment, housing 18 is manufactured from two clam-shell halves having a length equal to the final length of housing 18. In this first embodiment, the electronics are inserted between the two clam shells and the clam shells are welded together to form a hermetic seal. In the second embodiment, housing 18 is formed from two clam-shell halves which are slightly longer than the final length. These clam shells are welded together initially without the electronic assembly. The end portion is then removed, the electronics are inserted therein and a cap is welded over the opening to form a hermetic seal. In the one embodiment, lead 22 is a helical coil comprised of a medical grade metal alloy such as MP35N.

2. DC Configuration

Figure 3:
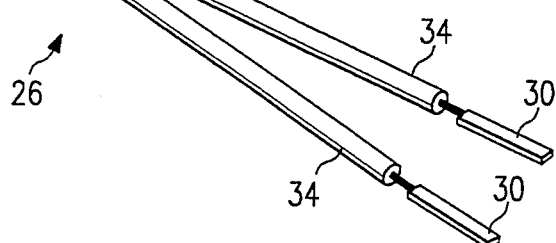
FIG. 3 is an isometric illustration of the disclosed bone growth stimulator configured for generating a direct current output.

FIG. 3 depicts an isometric illustration of the disclosed bone growth stimulator 26 configured for generating a direct current output (hereinafter the "DC stimulator"). DC stimulator 26 comprises an anode 28 and two cathodes 30. Anode 28 is a quantity of platinum electroplated onto the housing of DC stimulator 26 (shown substantially in FIG. 2). DC stimulator 26 has a short elastomeric arm 32 to better smooth DC stimulator 26 for insertion into the human body and to insulate the feed-through assembly (depicted in FIG. 2). As described in connection with FIGS. 1 and 2, DC stimulator 26 has a titanium housing. It is not coated with a non-conductive material. In addition, cathodes 30 are coupled to electronics within DC stimulator 26 by a coil manufactured from a suitable medical grade metal alloy such as MP35N. Leads 34 are not completely incased in arm 32 so that cathodes 30 may be more easily placed on or within the bone mass to be treated. Leads 34 are sheathed in a tube of elastomeric material.

In operation, DC stimulator 26 generates a DC current between cathodes 30 and anode 28. As will be described in connection with FIGS. 10 through 22, each cathode 30 of DC stimulator 26 is an independent current path.

B. OUTPUT CHARACTERISTICS

1. AC Configuration

Figure 4:
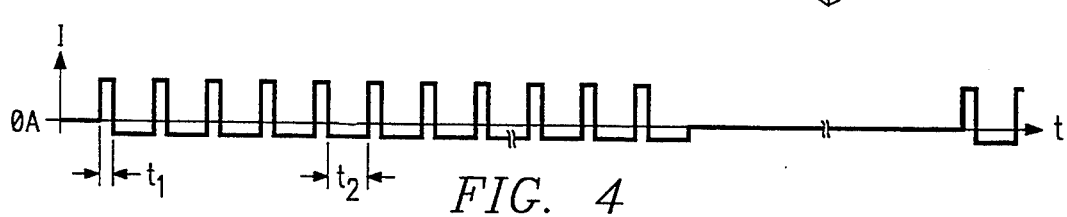
FIG. 4 is a graphical representation of the output of the bone growth stimulator depicted in FIGS. 1 and 2.

FIG. 4 is a graphical representation of the output of the bone growth stimulator depicted in FIGS. 1 and 2. AC stimulator 10 (depicted in FIGS. 1 and 2) generates an alternating current output. In the preferred embodiment, AC stimulator 10 generates an asymmetric output of 99 pulses (a "burst") followed by a rest period. After the rest period, the burst/rest cycle is repeated until AC stimulator 10 is turned off. The positive portion of the output pulse, indicated having the duration $t_1$, is approximately 65 $\mu$s long and has an amplitude of 900 $\mu$A. This current generates approximately 3 mV/cm at the healing site in implantation configuration depicted in FIG. 6. The negative portion of the output, indicated having the duration $t_2$, is approximately 195 $\mu$s long and has an amplitude of $-300$ $\mu$A. Thus generates $-1$ mV/cm at the same healing site. The AC output signal is off after 99 pulses for approximately 640 milliseconds. The resulting burst/rest rate has a frequency of 1.49 Hz.

It should be understood that AC stimulator 10 may be made to output other wave forms, both symmetric and asymmetric. For instance, AC stimulator 10 could produce a wave form having a sinusoidal form. The amplitude of the negative portion of the output may be modified to provide a field strength of $-0.3$ to $-3$ mV/cm at the bone site with a corresponding field strength of 0.9 to 9 mV/cm for the positive portion of the waveform, to keep the ratio between the positive portion and negative portion of the output at approximately three to one. This range produces optimum healing results.

2. DC Configuration

Figure 5:
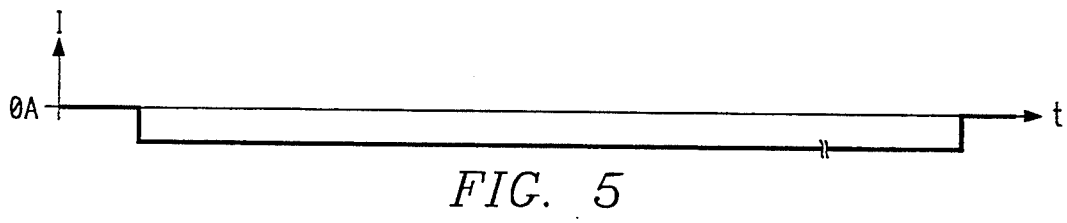
FIG. 5 is a graphical representation of the output of the bone growth stimulator depicted in FIG. 3.

FIG. 5 is a graphical representation of the output of the bone growth stimulator depicted in FIG. 3. DC stimulator 26 (shown in FIG. 3) generates a constant negative current between its two cathodes and anode of approximately $-20$ $\mu$A during its operation.

3. IMPLANTATION CONFIGURATION

1. AC Configuration

Figure 6:
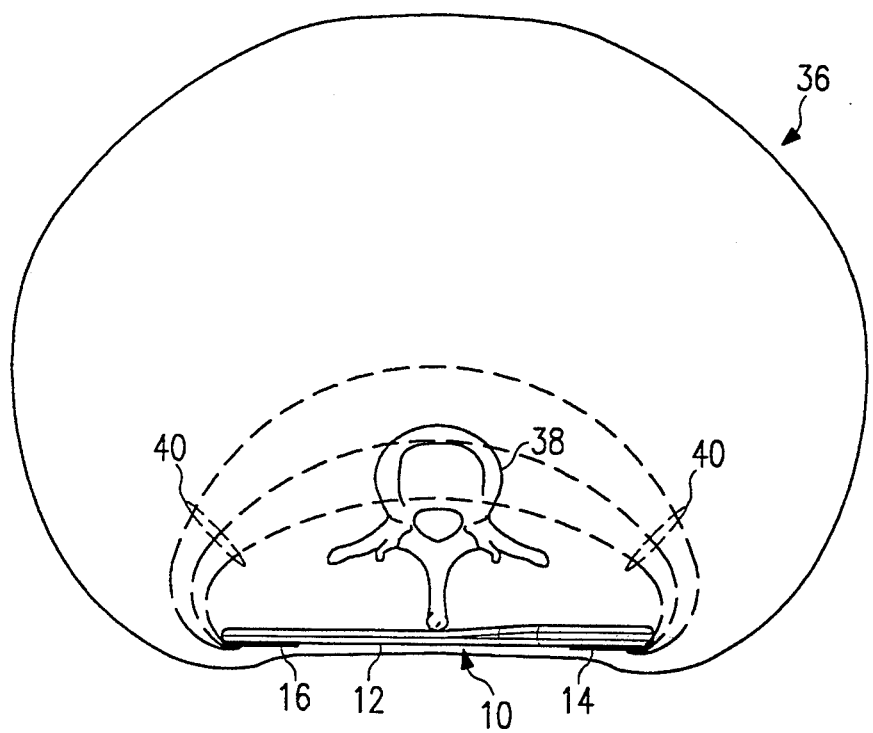
FIG. 6 is a simplified cross-sectional view of the human body depicting one embodiment of an implant configuration for the bone growth stimulator depicted in FIGS. 1 and 2.

FIG. 6 is a simplified cross-sectional view of the human body depicting one embodiment of an implant configuration for AC bone growth stimulator 10 depicted in FIGS. 1 and 2. AC stimulator 10 is bisected along its longitudinal axis in a plane generally perpendicular to the planes containing the electrodes 14 and 16. AC stimulator 10 is implanted in the human body indicated generally by 36 near a vertebra 38. AC stimulator 10 is placed near vertebra 38 so that the electric field generated between electrodes 14 and 16 is made to penetrate a portion of vertebra 38 in need of bone growth stimulation. The outer limit of the electric field generated by AC stimulator 10 is indicated generally by field lines 40. Vertebra 38 typically is in need of bone growth stimulation when two or more vertebrae are clinically fused together.

Because of the AC nature and the electrode spacing of AC stimulator 10, vertebra 38 will receive the benefit of the electric field 40 even if AC stimulator 10 does not abut vertebra 38. For instance, AC stimulator 10 may be placed further than 1 centimeter away from the injured section of vertebra 38. This allows a surgeon to implant AC stimulator 10 subcutaneously. This simplifies implant and explant, reduces the chance of infection and improves imaging results. Imaging results are improved because there are no foreign objects near vertebra 38.

In the preferred embodiment, AC stimulator 10 is implanted subcutaneously with its electrodes 14 and 16 facing away from vertebra 38. Empirical studies have determined that this placement results in a better electric field distribution and lower inadvertent muscle stimulation.

2. DC Configuration

Figure 7:
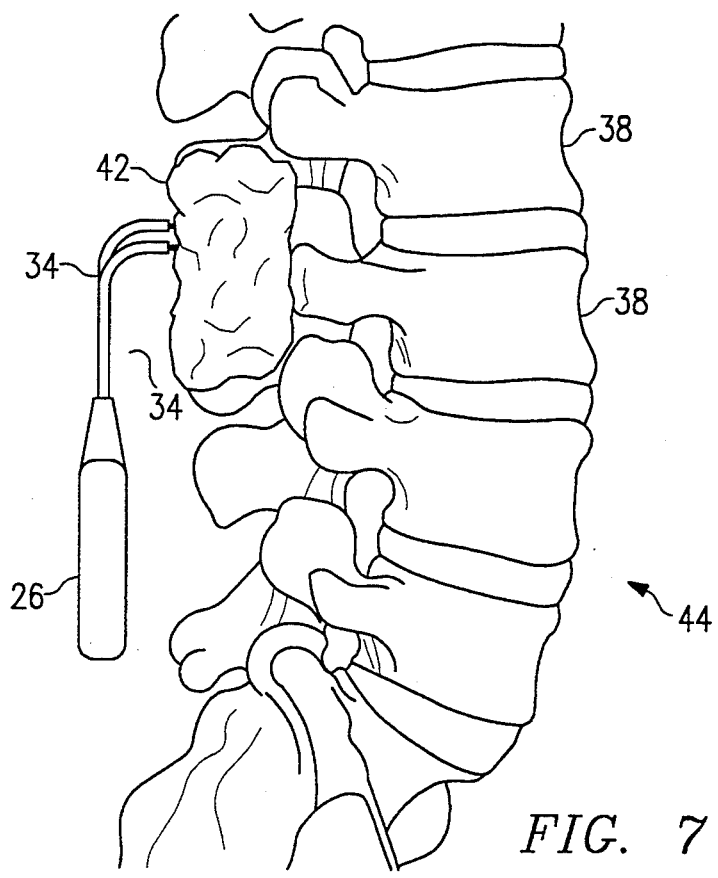
FIG. 7 is a simplified isometric view of the human body depicting one embodiment of an implant configuration for the bone growth :stimulator depicted in FIG. 3.

FIG. 7 is a simplified isometric view of the human body depicting one embodiment of an implant configuration for the DC stimulator 26 depicted in FIG. 3. Here, DC stimulator 26 is used to fuse a bone growth mass 42 to two adjacent vertebrae 38 of spine 44. DC stimulator 26 may be implanted subcutaneously. However, leads 34 must be inserted such that cathodes 30 (not shown) are directly in or adjacent to bone graft mass 42. It is not required that both cathodes 30 be placed at the same bone site.

It should be understood that both AC stimulator 10 and DC stimulator 26 may be implanted near any bone for the repair of several types of bone injuries. For instance, the stimulators may be used to promote bone healing in the long bones of the body. Also, the stimulators may be used at a bone site to promote the healing of a bone fracture.

D. ELECTRONIC IMPLEMENTATION

1. Overview

Figure 8A:
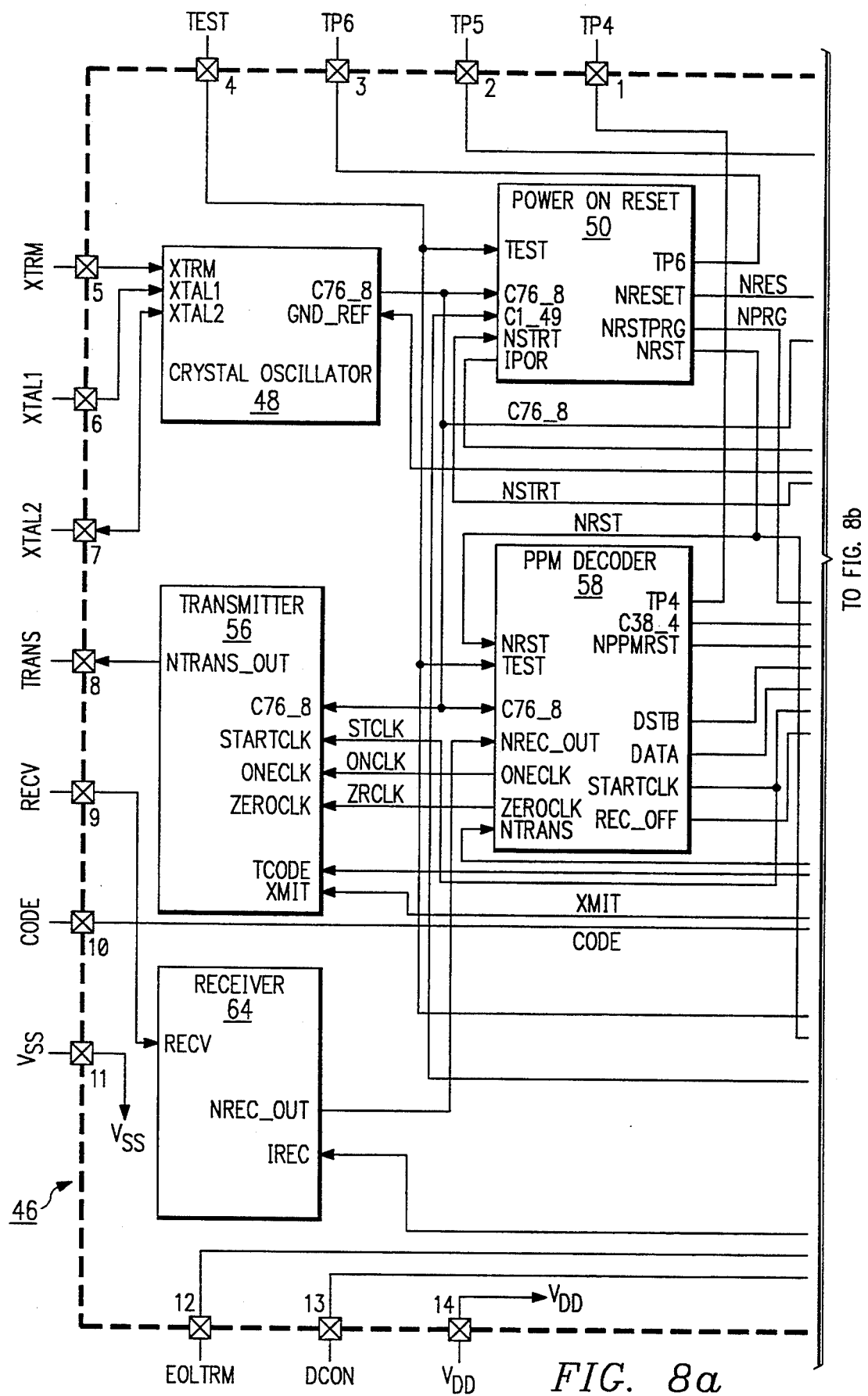

FIGS. 8a and 8b depict left and right halves of a block diagram of the application specific integrated circuit ("ASIC") 46 used in the bone growth stimulator depicted in FIGS. 1 through 3. Integrated circuit 46 has 28 external connections, pads 1 through 28. Internally, IC 46 comprises a crystal oscillator circuit 48, a power on reset circuit 50, a main time base circuit 52, an output driver circuit 54, a transmitter circuit 56, a PPM decoder circuit 58, a communication modem circuit 60, a lead status circuit 62, a receiver circuit 64, a battery status circuit 66, and a voltage reference/regulator circuit 68.

Crystal oscillator circuit 48 generates a 76.8 kHz clock signal labeled C76_8. This circuit has three external connections, XTRM, XTAL1, and XTAL2, and one input GND_REF. This circuit is more fully described in connection with FIG. 10.

Power on reset circuit 50 generates three reset outputs, NRESET, NRSTPRG, NRST, to put all other circuits in an initial condition after powering up. This circuit has four inputs, C76_8, C1_49, NSTRT and IPOR, and two test points, TEST and TP6. Power on reset circuit 50 is more fully described in connection with FIG. 11.

Main time base circuit 52 generates the pulse timing signals for control of the output driver circuit 54. In addition, main time base circuit 52 acts as the 24-hour timer for IC 46. This circuit generates 8 outputs, BIASON, NIPLUS, IMINUS, IMINUS2, NOUT_ON, NEN_ANL, ANL_CLK, and C1_49. This circuit has six inputs, NRESET, REC_OFF, C76_8, DCON, STIM0, STIM1, and two test points, TEST and TP1. Main time base circuit 52 is more fully described in connection with FIG. 12.

Output driver circuit 54 controls the output signal, OUT1 and OUT2 delivered to the patient. This circuit has inputs GND_REF, NOUT_ON, IMINUS, IMINUS2, NIPLUS, and BIASON and external connections ILIMIT, ITRM, and SYMTRM. Output driver circuit 54 is more fully described in connection with FIG. 13.

Transmitter circuit 56 combines the pulse timing parameters from PPM decoder 58 with the data output from communication modem 60 to transmit a low frequency magnetic pulse to an external receiver through NTRANS_OUT. This circuit has inputs C76_8, STARTCLK, ONECLK, ZEROCLK, TCODE and XMIT. Transmitter circuit 56 is more fully described in connection with FIG. 14.

PPM decoder circuit 58 determines if received information from receiver circuit 64 is a valid down-link communication. Also, PPM decoder circuit 58 generates the pulse position protocol used by transmitter circuit 56. This circuit has outputs C38_4, NPPMRST, DSTB, DATA, STARTCLK, REC_OFF, ZEROCLK, ONECLK. PPM decoder circuit 58 also has inputs C76_8, NREC_OUT, NTRANS, NRST, and 2 test points, TEST and TP4. This circuit is more fully described in connection with FIGS. 15a and 15b.

Communication modem circuit 60 controls the mode of operation of IC 46 through two of its output bits, STIM0 and STIM1. These two bits define the four possible modes of operation: off, four hours on/20 hours off, eight hours on/16 hours off, or continuously on. Also this circuit receives signals from battery status circuit 66 indicating the status of the battery (EOL and LOWBATT) and from lead status circuit 62 indicating the impedance of the output leads (LDHIGH and LDLOW). The circuit then generates an 11-bit communication word and transmit enable (TCODE and XMIT) for transmission by transmitter circuit 56. Communication modem circuit 60 circuit has eleven other inputs, NRSTPRG, C38_4, NPPMRST, DSTB, DATA, STARTCLK, REC_OFF, DCON, and CODE, two other outputs, NTRANS and NSTRT, and two test points, TEST and TP5. Communication modem circuit 60 is more fully described in connection with FIG. 16.

Lead status circuit 62 compares the impedance of the output leads with a predetermined threshold or thresholds. It has two outputs, LDLOW and LDHIGH. The circuit has inputs, NRST, IMINUS, ANL_CLK, DCON, NEN_ANL, ILEAD, and connections to OUT1, OUT2, LDTRM1 and LDTRM2, and two test points, TEST and TP2. Lead status circuit 62 is more fully described in connection with FIG. 17.

Receiver circuit 64 generates a digital output, NREC_OUT from an analog input RECV. This signal is received from a device external to IC 46. Receiver circuit 64 has an additional input IREC. This circuit is more fully described in connection with FIG. 18.

Battery status circuit 66 monitors the voltage supplied by the associated battery and signals the communication modem circuit 60 when the battery reaches two trippoints with LOWBATT and EOL. This circuit has inputs, NRST, REC_OFF, C1_49, NEN_ANL, IBATT, and GND_REF, an external connection to EOLTRM and two test points, TEST and TP3. Battery status circuit 66 is more fully described in connection with FIG. 19.

Voltage reference/regulator circuit 68 generates the bias currents used in IC 46: IPOR, IREC, IBATT, ILEAD, IDCON, ICODE, and ITEST. This circuit has inputs, VSET1, VSET2, and VREF and output GND_REF. Voltage reference regulator circuit 68 is more fully described in connection with FIG. 20.

2. Communications Protocol

FIG. 9a is a graphical representation of the communication protocol used by the circuit depicted in FIGS. 8a and 8b. Integrated circuit 46 transmits and receives data at 1200 Hz. This rate results in a 833 μs overall transmission window. After receiving a start pulse at the start window, integrated circuit 46 looks for the presence or absence of a data pulse in the "one window," "zero window" or "no pulse detected window". As depicted, these three data windows occur approximately 208 μsec, 416 μsec, and 624 μsec after the start pulse. The communication protocol results in a data logic level one if a pulse is received in the one window and a data value zero if a pulse is received in the zero window. A communications error is indicated if a pulse is received in the no pulse detected window. The disclosed communications protocol permits additional error checking by requiring a pulse at both start windows and requiring one but not both of the one window and zero window to have a data value. Each window is approximately 104 μs long. Data detection is enabled only in the four windows described above during each communication.

An external receiver/transmitter may be fabricated from a microprocessor with 1200 Baud capability connected to a suitable coil.

FIGS. 9b and 9c depict tables containing an explanation of the down-link program data word and up-link handshake respectively of the circuit depicted in FIGS. 8a and 8b. Integrated circuit 46 uses an 11 bit program data word. The down-link, or received data word comprises three programmable data bits. The second, third, and fourth bits of the down link program data word contain data which is used by integrated circuit 46 to adjust its mode of operation. Bit 2 is a read-not write (RNW) bit. When RNW equals zero, IC 46 acts upon the third and fourth bits as subsequently described. If RNW equals one, then IC 46 will simply up-link an 11 bit program data word to the external transmitter/receiver. The third and fourth bits, STIM0 and STIM1 indicate how long the bone growth stimulator runs. As depicted in FIG. 9a, the bone growth stimulator has four modes of operation. (1) It may be continuously off. (2) It may be on 4 hours, off 20 hours. (3) It may be on 8 hours, off 16 hours. (4) It may operate continuously. All other bits in the down link program data word do not vary. The first, sixth, and seventh bits must be a logic 1 while the fifth, eighth, and eleventh bits must be a 0. The ninth and tenth bits must follow the hard-wired control bits DCON and CODE respectively. DCON is an externally hard-wired bit indicating whether the bone growth stimulator is configured for AC or DC output. A logical level of 0 indicates an AC output while a logic level of 1 indicates a DC output. CODE is an externally hardwired input bit. It may be used, for instance, to indicate a first and second version of manufactured stimulators. The down-link program data word is transmitted left to right.

The up-link program data word transmitted from integrated circuit 46 to an external receiver has 8 bits of data, an odd parity check, and start and stop bits. The start and stop bits are logic high and low respectively. The second and third bits indicate the present mode of operation of IC 46 as described in connection with the down-link program data word. The fourth and fifth bits indicate whether the DCON or CODEs bits are high or low. The sixth and seventh bits indicate the status of the stimulator leads. In the AC mode, these bits indicate whether electrode 16 (shown in FIGS. 1 and 2) is normal, has a low impedance or has a high impedance. In the DC mode, these bits indicate whether either of leads 34 (shown in FIG. 3) has an abnormally high impedance. The particular logic values for each condition in each mode is defined in this FIGURE. The eighth and ninth bits indicate the status of the internal battery of the bone growth stimulator. The battery status circuitry 62 (depicted in FIG. 8) monitors the battery voltage for two trippoints, 2.1 V and 2.4 V. These voltages correspond to the end of life (EOL) and low battery (LOWBATT) depicted as indicated in the FIGURE. The tenth data bit is an odd parity check bit. It is high when the number of ones preceding it is even and it is low when the number of ones preceding it is odd.

3. Signal/External Input Description

The following signals are used by integrated circuit 46 internally and as external connections:

ANL_CLK is generated by main time base circuit 52. It enables lead status circuit 62 during certain intervals of the DC output signal.

BIASON is generated by the main time base circuit 52. In the AC mode, it turns on the bias current for the positive portion of the output signal. It is disabled during the negative portion of the AC signal output. In the DC mode, it is continuously high. BIASON is used by the output driver.

C1_49 is generated by main time-base circuit 52. It is a clock signal of 1.49 Hz. It is used as a gating signal for the control logic of the output switches of output driver 54.

C76_8 is generated by crystal oscillator circuit 48. It is a clock signal of 76.8 kHz. It is the main time signal used by integrated circuit 46.

CODE is an externally hardwired input bit (Pad 10). The communication protocol requires that communication words have a matching bit for a valid downlink.

DATA is generated by PPM decoder block 58. It is the output from the PPM decoder indicating a valid data 0 or data 1 received from receiver circuit 64.

DCON is an externally hardwired bit (Pad 13). It is used to indicate for which configuration, AC or DC, the circuit is set up. A logic level of 0 indicates the AC configuration while logic level 1 indicates DC configuration.

DSTB is generated by PPM decoder circuit 58. It strobes valid data into communication modem circuit 60.

EOL is generated by battery status circuit 66. This bit will have a logic value of 1 when the battery voltage is less than or equal to 2.1 V. Otherwise it will have a logic value of 0.

EOLTRM is an input to battery status circuit 66. It is coupled to $V_{DD}$ through an external capacitor and resistor (Pad 12). It is used to trim the low battery and end of life voltages to the desired trippoints (here, 2.4 and 2.1 V respectively).

GND_REF is generated by voltage reference/regulator circuit 68. It is a buffered voltage level, 1.5 V less than $V_{DD}$. It is brought off-chip through pad 18.

IBATT is generated by voltage reference regulator circuit 68. It produces a 20 nA current sink used to establish the bias current in battery status circuit 68.

ICODE is generated by the voltage reference/regulator circuit 68. It produces a 100 nA current sink used to pull down the CODE pin if that pin is left open.

IDCON is generated by voltage reference/regulator circuit 68. It produces a 100 nA current sink used to pull down the DCON pin if that pin is left open.

ILEAD is generated by voltage reference/regulator circuit 68. It is a 20 nA current source used to bias lead status circuit 62.

ILIMIT is an external connection to output driver circuit 54 (Pad 22). In the AC mode, ILIMIT is not used. In the DC mode, ILIMIT is connected to the stimulator housing and acts as the unit anode.

IMINUS is generated by main time base circuit 52. In the AC mode, it switches the negative output portion of the signal. In the DC mode, it switches the output current. It is used by output driver circuit 54.

IMINUS2 is generated by main time base circuit 52. In the AC mode, it is not used. In the DC mode, it switches the output current for OUT2. It is used by output driver circuit 54.

IPOR is generated by voltage reference/regulator circuit 68. It is a 10 nA current sink used to bias the power on reset circuit 50.

IREC is generated by voltage reference/regulator circuit 68. It is a 20 nA current source used by the receiver circuit 64.

ITEST is generated by the voltage reference/regulator 68. It is a 100 nA current sink used to pull down the TEST pin if that pin is not connected.

ITRM is an external connection to $V_{DD}$ through an external resistor (Pad 25). The resistor is used to trim the output current in both the AC and DC modes. It is an input to output driver circuit 54.

LDHIGH is generated by the lead status unit. In the AC mode, a logic level 1 indicates a high lead impedance. In the DC mode, a logic level 1 indicates a high lead impedance for OUT2.

LDLOW is generated by the lead status unit. In the AC mode, a logic level of 1 indicates a low lead impedance. In the DC mode, logic level of 1 indicates a high lead impedance for OUT1.

LDTRM1 is an input to lead status circuit 62. It is coupled to GND_REF through an external resistor (Pad 20). It sets the trippoints for lead status circuit 62.

LDTRM2 is an input to lead status circuit 62. It is coupled to GND_REF through two resistors in series (Pad 19). It is used to set the trippoints for lead status circuit 62.

LOWBATT is generated in battery status circuit 66. This signal is normally low. When the battery output drops below 2.4 V, this signal switches to logic level 1.

NEN ANL_ is generated by main time base unit 52. In the AC mode, this signal enables the battery and lead status circuits during the negative portion of the output signal. Otherwise, these circuits are disabled to conserve power. In the DC mode, this signal enables the battery and lead status circuits once every 1.49 Hz.

NIPLUS is generated by main time base circuit 52. In the AC mode, this signal controls the output switch for the positive portion of the output signal. It is not used in the DC mode.

NOUT_ON is generated by main time base circuit 52. In the AC mode, this signal enables the output driver during the burst period. It is otherwise off. In the DC mode, this signal is on for the duration of the stimulus, i.e., 4 hours, 8 hours, or continuous.

NPPMRST is generated by PPM decoder circuit 58. It is a primary reset for the communication modem circuit 60.

NREC_OUT is generated by the receiver circuit 64. It is a digital representation of the received external input.

NRESET is generated by power on reset circuit 50. It is reset on power up and after a valid downlink/uplink communication. In either case, it returns high after two 76.8 kHz clock cycles.

NRST is generated by power on reset circuit 50. It is reset on power up and after a valid downlink/uplink communication. In either case, it returns to its high state after one 1.49 Hz clock cycle.

NRSTPRG is generated by power on reset circuit 50. It is reset on power up. It returns to its high state after NRST transitions high.

NSTRT is generated by communication modem circuit 60. It initiates a reset after a valid downlink/uplink communication.

NTRANS is generated by communication modem circuit 60. It indicates the completion of a valid downlink communication.

NTRANS_OUT is generated by transmitter unit 58. It is the output signal of the driver stage of the transmitter circuit 56. It is connected to an external coil (Pad 8).

ONECLK is generated by PPM decoder circuit 58. It is the decoded clock signal corresponding to the data position for logic level one in the communications protocol.

OUT1 is an output from output driver circuit 54 (Pad 23). In the both the AC and DC modes, this is the output signal.

OUT2 is an output from output driver circuit 54 (Pad 24). In the AC mode, OUT2 is connected to OUT1. In the DC mode, OUT2 is the second independent current path.

REC_OFF is generated by PPM decoder circuit 58. This signal disables the receiver, battery status and output driver circuits during an uplink operation.

RECV is input to receiver unit 56. It is coupled to an external coil (Pad 9).

STARTCLK is generated by PPM decoder circuit 58. It is a decoded clock signal corresponding to the start position in the communications protocol.

STIM0 is generated by communication modem circuit 60. It is used with the STIM1 bit to generate the four stimulation modes (off, on 4 hours, on 8 hours, on continuously).

STIM1 is generated by communication modem circuit 60. It is used with the STIM0 signal to generate the four stimulation modes (off, on 4 hours, on 8 hours, on continuously).

SYMTRM is an input to output driver circuit 54. It may be coupled to GND_REF or $V_{DD}$ through an external resistor (Pad 21). It is used to trim the positive portion of the output current. It is presently not used.

TCODE is generated by communication modem circuit 60. It is the data output sent to transmitter circuit 56 for external transmission.

TEST is a testing signal used in conjunction with TP1 through TP6. It is brought off chip at pad 4.

TP1 through TP6 are external test points (Pads 26, 27, 28, 1, 2, and 3 respectively). They output data from the various cell blocks for testing purposes.

$V_{DD}$ is an external connection to the positive terminal of the 2.8 V battery (Pad 14).

$V_{SS}$ is an external connection to the negative terminal of the 2.8 V battery (Pad 11).

VREF is an input to voltage reference/regulator circuit 68. It is coupled to a 1.5 V unbuffered reference voltage (Pad 17).

VSET1 is an input to voltage reference/regulator circuit 68. It is coupled to $V_{DD}$ through two external resistors in series (Pad 15). It is used to trim VREF.

VSET2 is an input to voltage reference/regulator circuit 68. It is coupled to $V_{DD}$ through a resistor (Pad 16). It is also used to trim VREF.

XMIT is generated by communication modem circuit 60. It enables the transmitter output.

XTAL1 is an external connection to one terminal of a 76.8 kHz oscillator/resistor circuit (Pad 6). It is an input to crystal oscillator circuit 48.

XTAL2 is an external connection to one terminal of a 76.8 kHz oscillator/resistor pair (Pad 7). It is an input to crystal oscillator circuit 48.

XTRM is an external connection to $V_{DD}$ through a resistor (Pad 5). It sets the bias current on the 76.8 kHz crystal oscillator.

ZEROCLK is generated by PPM decoder circuit 58. It is the decoded clock signal corresponding to a logic level zero in the communications protocol.

4. Circuit Description a. Crystal Oscillator

Figure 10:
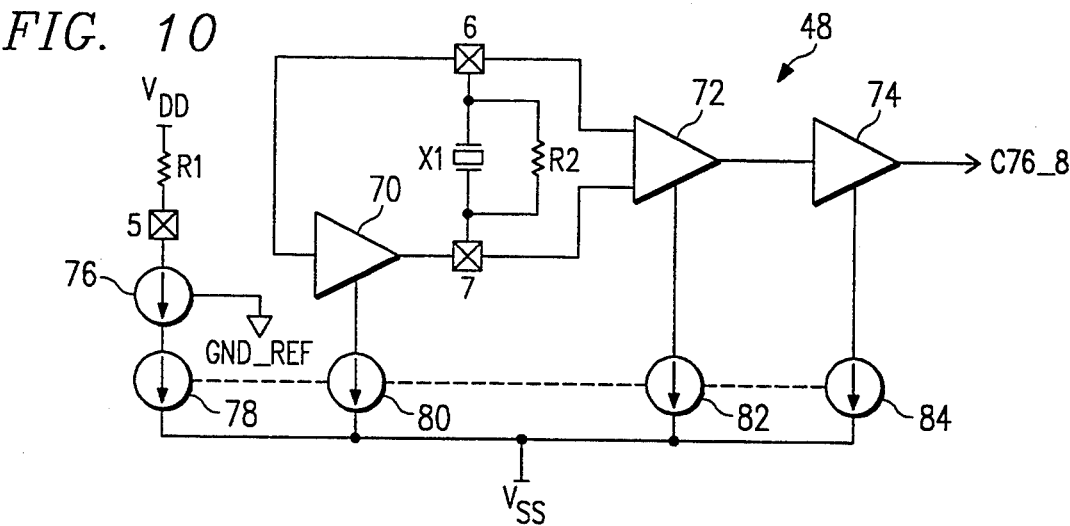

FIG. 10 illustrates a block diagram of the crystal oscillator circuit 48 depicted in FIG. 8a. Crystal oscillator circuit 48 comprises a crystal driver 70, a hysteresis comparator 72, and an output driver 74. Crystal driver 70 is connected to crystal X1 and resistor R2 through pads 6 and 7. Crystal X1 and resistor R2 are themselves connected in parallel. The inputs of hysteresis comparator 72 are also coupled to crystal X1 and resistor R2 through pads 6 and 7. The output of hysteresis comparator 72 is connected to output driver 74 which outputs signal C76_8. An external resistor R1 is coupled between $V_{DD}$ and pad 5. Pad 5 is coupled to two current sources 76 and 78 in series. Current source 76 is controlled by the signal GND_REF. Current mirrors 80, 82, and 84 supply the bias current to crystal driver 70, hysteresis comparator 72, and output driver 74, respectively. Each of these current mirrors mirror current source 78 times some integer. This relationship is indicated by the dashed line. In particular, current mirror 80 sources a current five times that of current source 78, current mirror 82 sources three times the amount of current sourced by current source 78 and current mirror 84 sources two times the current of current source 78. Current source 78 and current mirrors 80, 82 and 84 are connected to $V_{SS}$.

In operation, crystal driver 70 applies a voltage across crystal X1 such that crystal X1 oscillates at the regular frequency of 76.8 kHz. Hysteresis comparator 72 toggles if the potential across crystal X1 swings approximately 100 mV. The digital high low output of hysteresis comparator 72 is amplified by output driver 74. Driver 74 ensures that the final signal swings rail to rail ($V_{SS}$ to $V_{DD}$). Resistor R1 in conjunction with GND_REF is used to adjust the bias current mirrors 80, 82, and 84.

b. Power On Reset

Figure 11:
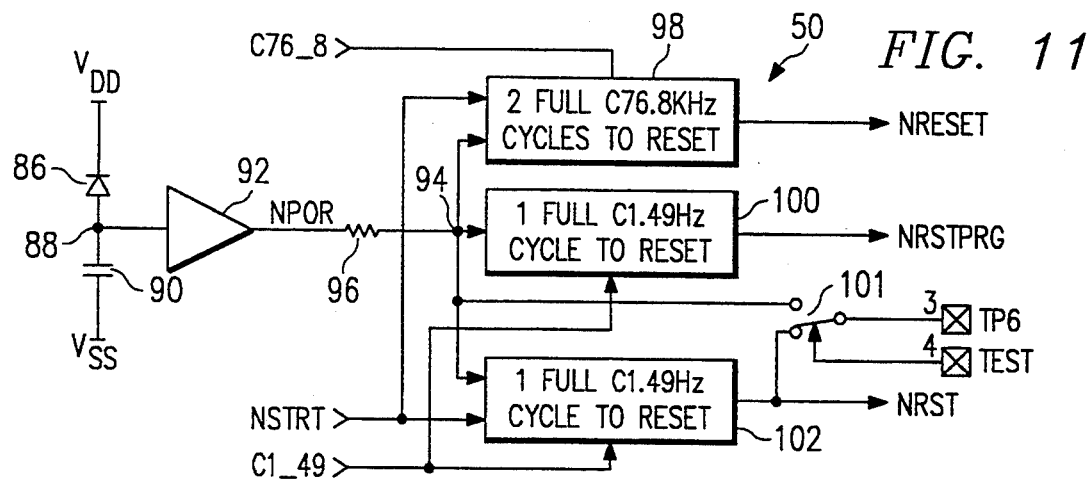

FIG. 11 illustrates a block diagram of the power on reset circuit 50 depicted in FIG. 8a. Power on reset circuit 50 comprises a diode 86 connected between $V_{DD}$ and a node 88. Node 88 is coupled to $V_{SS}$ through a capacitor 90. Capacitor 90 may have a capacitance of 6 pF. Node 88 is coupled to the input of a buffer 92. Buffer 92 is coupled to a node 94 through a 10 kOhm resistor 96. Node 94 acts as one input to latches 98, 100, and 102. Latches 98 and 102 are dual reset latches, while latch 100 is a single reset latch. Latch 98 gets set (NRESET goes high) two 76.8 kHz clock cycles after both reset conditions (NPOR, node 94, is low or NSTRT is low) return to logic one. Similarly, latch 102 gets set one 1.49 Hz cycle after both reset conditions go high. Latch 100 gets set one 1.49 Hz cycle after reset condition NPOR goes high. As depicted, the outputs of latches 98, 100, and 102 generate signals NRESET, NRSTPRG, and NRST respectively.

TP6 is connected through pad 3 to either node 94 or NRST. The particular connection is dependant upon the logic level of TEST applied at pad 4. When TEST equals zero, TP6 is connected to NRST. When TEST equals one, TPC is connected to node 94.

In operation, a power drop will cause capacitor 90 to discharge. This will momentarily bring node 88 low. Buffer 92 will reset latches 98, 100, and 102. Latch 98 will return high after two full clock cycles of the clock signal C76_8. Latches 100 and 102 will return high after one cycle of the clock signal C1_49. In addition, latches 98 and 102 may be reset by NSTRT.

During testing, TP6 views the output of slow buffer 92 at node 94 or the output of latch 102. Resistor 96 prevents TP6 from pulling down the output of buffer 92 during testing.

c. Main Time Base

Figure 12:
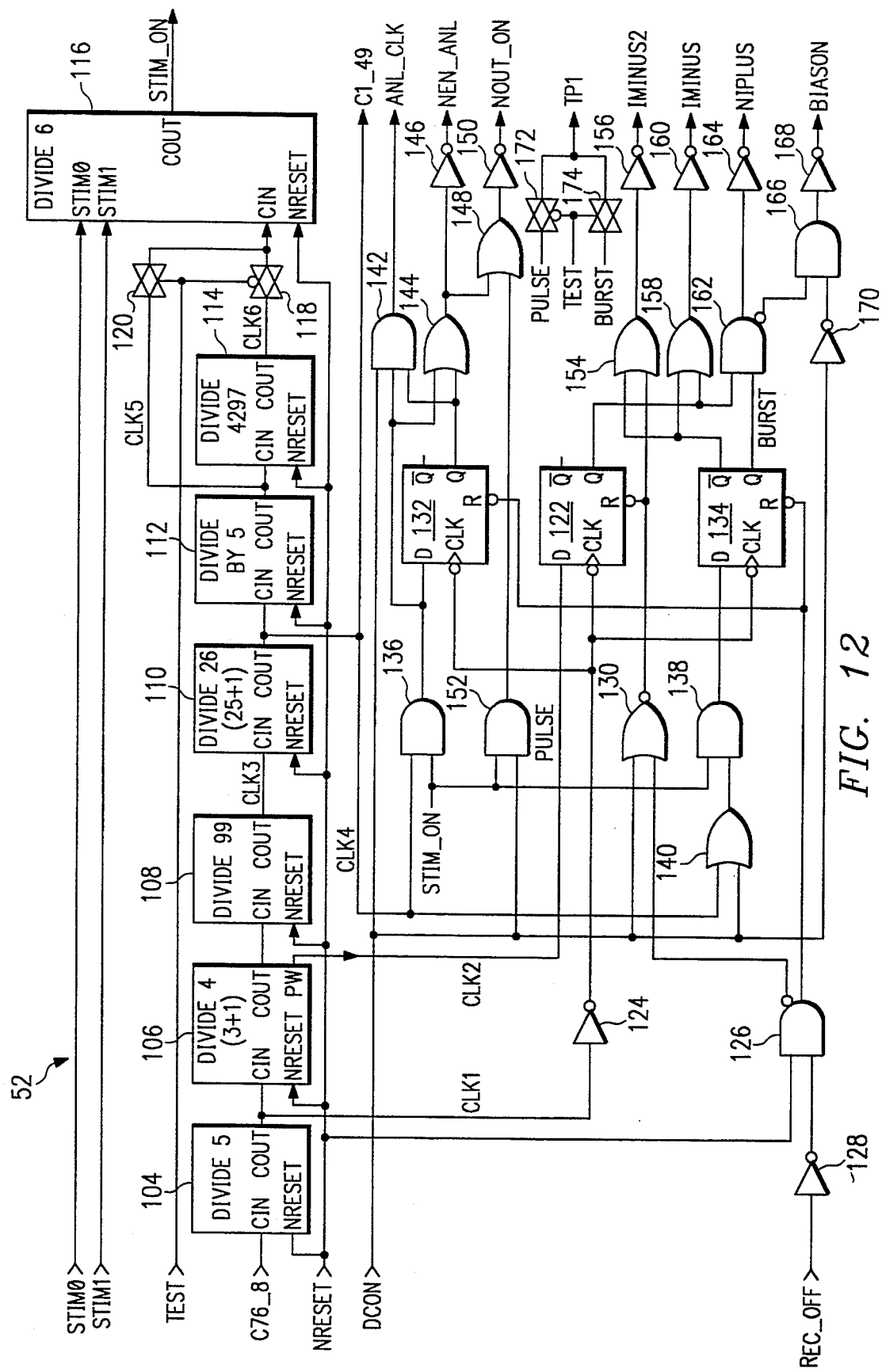
FIG. 12 illustrates schematically the main time base circuit depicted in FIG. 8b.

FIG. 12 illustrates schematically the main time base circuit 52 depicted in FIG. 8b. Main time base circuit 52 generates the clock signals necessary for output driver circuit 54 (shown in FIG. 13). Main time base circuit 52 comprises a series of cascaded divide-by circuits 104, 106, 108, 110, 112, 114, and 116 and various logic gates driven by the divide-by circuits. Each divide-by circuit lowers the frequency of the clock signal input to it by particular value. Divide-by circuit 104 is a divide-by 5 circuit which has as an input signal C76_8. Divide-by circuit 104 therefore outputs a 15.36 kHz signal. The output of divide-by circuit 104 is connected to the input of divide-by circuit 106. Divide-by circuit 106, a divide-by 4 circuit, generates a 3.84 kHz output. The output of divide-by circuit 106 is connected to the input of divide-by circuit 108. Divide-by circuit 108, a divide-by 99 circuit, generates a 38.8 Hz clock signal. The output of divide-by circuit 108 is input to the divide-by circuit 110. Divide-by circuit 110, a divide-by 26 circuit, generates a 1.49 Hz signal, C1_49. The output of divide-by circuit 110 is input to divide-by circuit 112. Divide-by circuit 112, a divide-by 5 circuit generates a clock signal having a period of 3.35 seconds. The output of divide-by circuit 112 is input to divide-by circuit 114. Divide-by circuit 114, a divide-by 4,297 circuit, generates a clock signal having a period of 4 hours. The output of divide-by circuit 114 is input, to divide-by circuit 116 through T-gate 118. Divide-by circuit 116, a divide-by 6 circuit, generates a clock signal having a period of 24 hours. Divide-by circuit 116 may alternately have as its input the output from divide-by circuit 112. The signal, CLK5 may be fed through T-gate 120 as depicted. T-gates 118 and 120 are controlled by TEST. Divide-by circuit 116 also has as its inputs signals STIM0 and STIM1. As depicted, each divide-by circuit 104 through 116 is reset by the signal NRESET.

The control logic of main time base circuit 52 generates the signals ANL_CLK, NEN_ANL, NOUT_ON, IMINUS2, IMINUS, NIPLUS and BIASON as depicted. C1_49 is the output of divide-by circuit 110. The output of divide-by circuit 104 clocks D-type flipflops 122, 132 and 134. The output of divide-by circuit 104 is first inverted by an inverter 124 before clocking flipflop 122. The input of flipflop 122, PULSE, is connected to an alternate output (PW) of divide-by circuit 106. Output PW, labeled CLK2, generates a pulse identical to the output of divide-by circuit 106 occurring on the falling edge of the output of divide-by circuit 106. NRESET and REC_OFF are input to an AND/NAND gate 126 after REC_OFF is inverted by an inverter 128. The nanded output of gate 126 is combined with DCON by a NOR gate 130. The output of gate 130 is connected to the RESET input of flipflop 122. The ANDed output of gate 126 is connected to the reset input of a D-type flipflops 132 and 134. Flipflop 132 has as its input the output of an AND gate 136. Gate 136 has two inputs, STIM_ON (the output of divide-by circuit 116) and the output from divide-by circuit 110. The input to flipflop 134 is connected to the output of an AND gate 138. Gate 138 has as its two inputs STIM_ON and the output from an OR gate 140. OR gate 140 has two inputs, DCON and the output from divide-by circuit 110.

ANL_CLK is the output from a three input AND gate 142. Gate 142 has inputs DCON, the output of gate 136 and the output of flipflop 132. NEN ANL is generated from the output of an OR gate 144 inverted by an inverter 146. OR gate 144 has inputs which are the outputs of gate 136 and flipflop 132. NOUT_ON is generated by the output of an OR gate 148 inverted by an inverter 150. Gate 148 has inputs which are the outputs of OR gate 144 and of an AND gate 152. Gate 152 has two inputs STIM_ON and DCON. IMINUS2 is generated from the output of an OR gate 154 inverted by an inverter 156. Gate 154 has inputs which are the outputs of flipflop 134 (inverted) and gate 130. IMINUS is generated from the output of an OR gate 158 inverted by an inverter 160. Gate 158 has inputs which are the outputs of flipflop 134 (inverted) and flipflop 122. NIPLUS is generated from the ANDed output of a dual AND/NAND gate 162 inverted by an inverter 164. Gate 162 has as its inputs the outputs from flipflops 122 and 134. BIASON is generated by the output of an AND gate 166 inverted by inverter 168. Gate 166 has as its input the nanded output of gate 162 and DCON inverted by an inverter 170.

In addition, T-gates 172 and 174 have their outputs coupled to TP1. The input of T-gates 172 and 174 are coupled to the alternate output, PW, of divide-by circuit 106 and the output of flipflop 134, respectively. T-gates 172 and 174 are controlled by TEST. When TEST equals 0, TP1 is connected to output PW of divide-by circuit 106. When TEST equals 1, TP1 is connected to the output of flipflop 134.

In operation, the output of divide-by circuit 116 (STIM_ON) generates a series of four-hour PULSES depending upon the values of STIM1 and STIM0 according to the following values: If STIM1=0 and STIM0=0, then STIM_ON is low continuously, if STIM1=0 and STIM0=1 then STIM_ON is periodically high for 4 hours and low for 20, if STIM1=1 and STIM0=0, then STIM_ON is periodically high for 8 hours and low for 16, if STIM1=1 and STIM0=1, then STIM_ON is continuously high. This internal signal controls the four modes of operation of the stimulator. The output of divide-by circuit 104 acts as the timing clock for main time base circuit 52. The alternate output, PW, of divide-by circuit 106 generates the 25% high/75% low duty cycle in the AC mode. Divide-by circuit 108 generates 99 PULSES for each burst of the AC signal. Divide-by circuit 110 generates the burst to rest ratio of 1:25. This is the 1.49 Hz output in the AC mode.

The final divide-by operations are split among three divide-by circuits 112, 114 and 166 to facilitate testing. This allows main time base circuit 52 to be tested using an artificial 20-second day. As described above, when TEST=1 the divide-by circuit 114 is bypassed. Also, as described above, the output of divide-by circuit 106 and flipflop 134 may be viewed directly through T-gates 172 and 174 through TP1.

d. Output Driver

Figure 13:
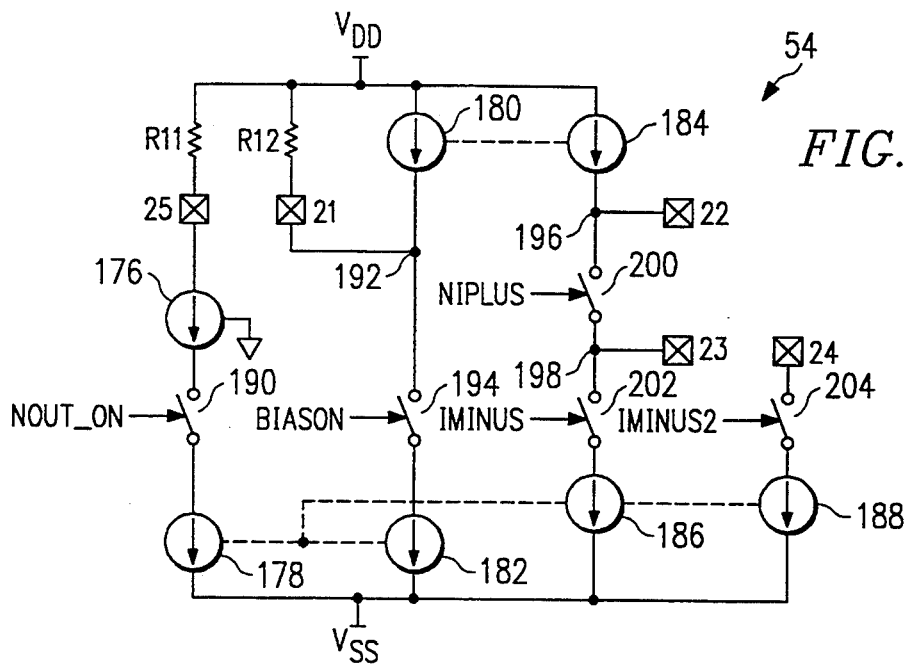
FIG. 13 illustrates a block diagram of the output driver circuit depicted in FIG. 8b.

FIG. 13 illustrates a block diagram of the output driver circuit 54 depicted in FIG. 8b. Output driver 54 comprises current mirrors 176, 178, 180, 182, 184, 186, and 188. Current mirror 176 is connected to $V_{DD}$ through pad 25 and an external resistor R11. Current mirror 176 has a control voltage input, GND_REF. Current mirror 176 is connected to current mirror 178 through a switch 190. Switch 190 is controlled by NOUT_ON. Current mirror 178 mirror is connected between switch 190 and $V_{SS}$. Current mirror 180 is connected between $V_{DD}$ and node 192. Node 192 is connected to $V_{DD}$ also through an optional external resistor R12 at pad 21. Node 192 is also connected to current mirror 182 through a switch 194. Switch 194 is controlled by BIASON. Current mirror 182 is also connected to $V_{SS}$. Current mirror 184 is connected between $V_{DD}$ and a node 196. Node 196 is connected externally to ILIMIT, at pad 22. Node 196 is also coupled to a node 198 through a switch 200. Switch 200 is controlled by NIPLUS. Node 198 is connected externally to OUT1, at pad 23 and to control mirror 186 through a switch 202. Switch 202 is controlled by IMINUS. Control mirror 186 is also connected to $V_{SS}$. A switch 204 is controlled by IMINUS2 and connects an external output, OUT2, at pad 24 to current mirror 188. Current mirror 188 is also connected to $V_{SS}$.

Resistor R11 trims the current through current mirror 176 and hence the current through current mirror 178. Current mirror 182 is designed such that it sinks three times the current of current mirror 178. Current mirrors 186 and 188 are designed such that they sink 33 times the current of current mirror 178. Current mirror 180 sources the same current as current mirror 182 when resistor R12 is omitted. Resistor R12 may be included to trim the current through current mirror 180. Current mirror 184 is designed such that it sources 33 times the current through current mirror 180 or approximately 99 times the current of current mirror 178.

In the AC mode of operation, switch 204 is open allowing OUT2 to be externally connected to OUT1.

Simultaneously, switches 200 and 202 are asymmetrically open and closed to periodically source and sink current to OUT1 from current sources 184 and 186. BIASON disables current mirrors 180 and 184 during the negative portion of the output. NOUT_ON enables output drive circuit 54 only during the pulse portion of the output signal. ILIMIT is not used.

In the DC mode of operation, ILIMIT is connected to the bone growth stimulator housing (depicted in FIG. 2) and acts as the anodes. Switch 200 is open and switch 194 is closed. OUT1 and OUT2 are connected to the 2 cathodes (depicted in FIG. 3) and each is connected to current mirrors 186 and 188, respectively, by switches 202 and 204, respectively. The DC output is controlled by IMINUS and IMINUS2.

e. Transmitter

Figure 14:
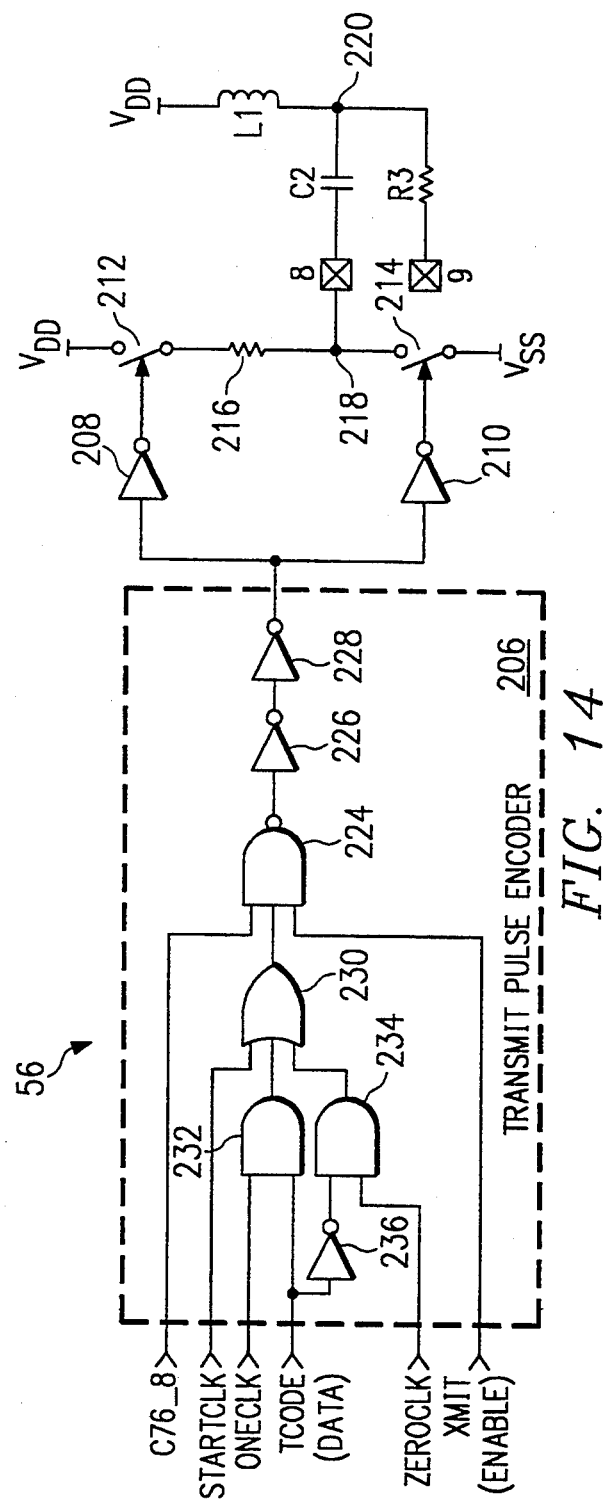

FIG. 14 illustrates schematically the transmitter circuit 56 depicted in FIG. 8. Transmitter circuit 56 comprises switching logic 206 which drives inverter drivers 208 and 210. Inverter drivers 208 and 210 control switches 212 and 214, respectively. Switch 212 connects $V_{DD}$ to a resistor 216. Resistor 216 is connected to a node 218. Switch 214 connects node 218 to $V_{SS}$. Node 218 is connected to a node 220 through an external connection, TRANS, at pad 8 through an external capacitor C2. Node 220 is connected to $V_{DD}$ through an external inductor L1. Also, node 220 is connected through an external resistor R3 back into integrated circuit 46 through RECV, at pad 9.

In one embodiment of transmitter circuit 56, resistors 216 and R3 are 10 kOhm resistors, C2 is a 1000 pF capacitor, and inductor L1 is a 4.8 mH inductor.

Logic 206 outputs to inverter drivers 208 and 210 the output of a NAND gate 224 twice inverted by inverters 226 and 228. Gate 224 is a three input NAND gate which combines C76_8 the output from an OR gate 230, and XMIT. Gate 230 is a three input OR gate having inputs STARTCLK, the output of an AND gate 232 and the output from an AND gate 234. Gate 232 has inputs ONECLK and TCODE. Gate 234 has inputs TCODE inverted by an inverter 236 and ZEROCLK.

In operation, logic 206 synchronizes output data on TCODE with the appropriate communications protocol window. In particular, a high data bit is synchronized with ONECLK and C76_8. A data low is synchronized with ZEROCLK and C76_8. XMIT acts as an enabling signal. The synchronized output signal from logic 206 will cause inverter 208 and 210 to close switches 212 and 214. Current will then flow through inductor 222. Logic 206 will peck inductor L1 twice per data bit due to the length of the pulses of the clocking signals and of TCODE.

f. PPM Decoder

Figure 15A:
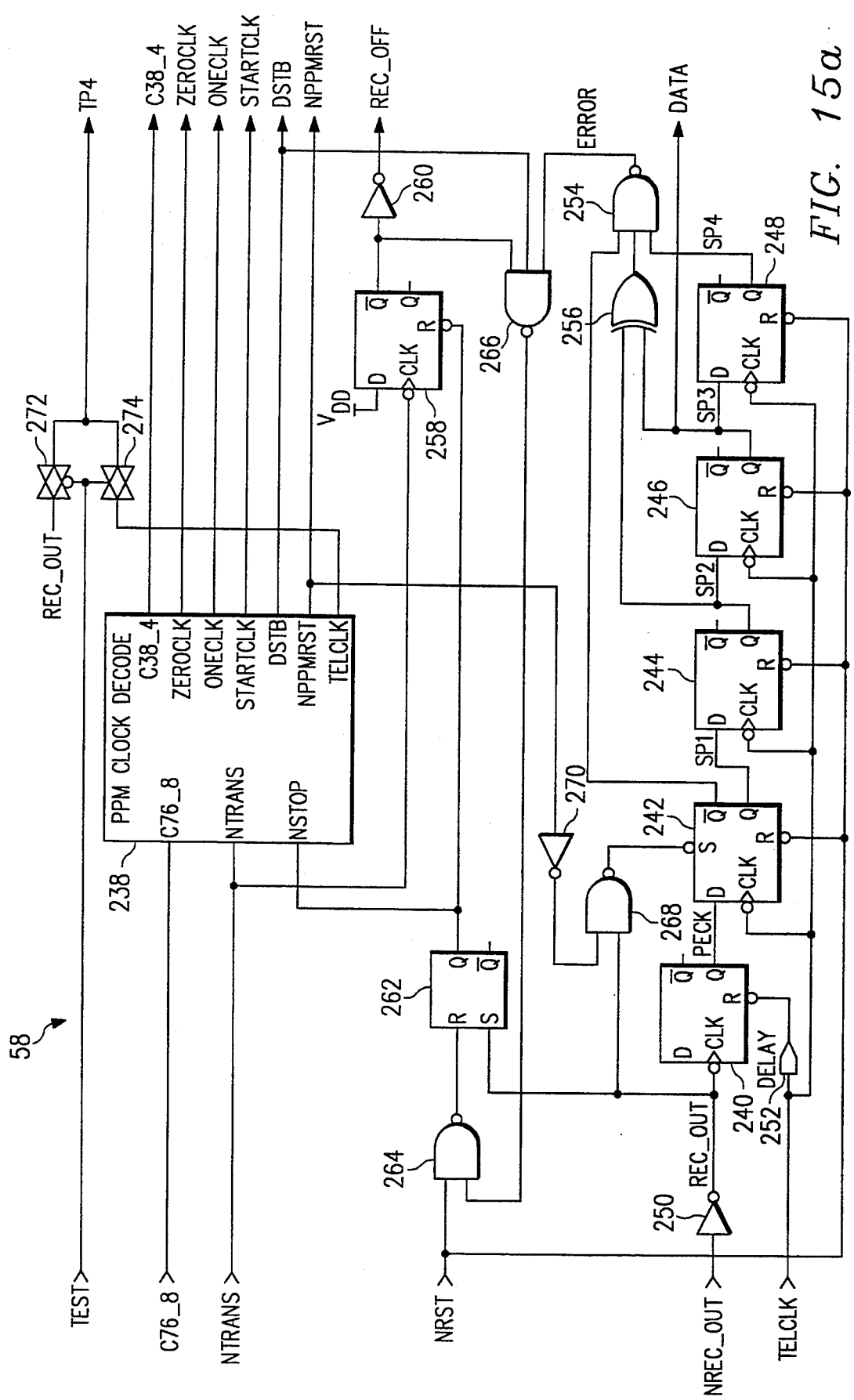
Figure 15B:
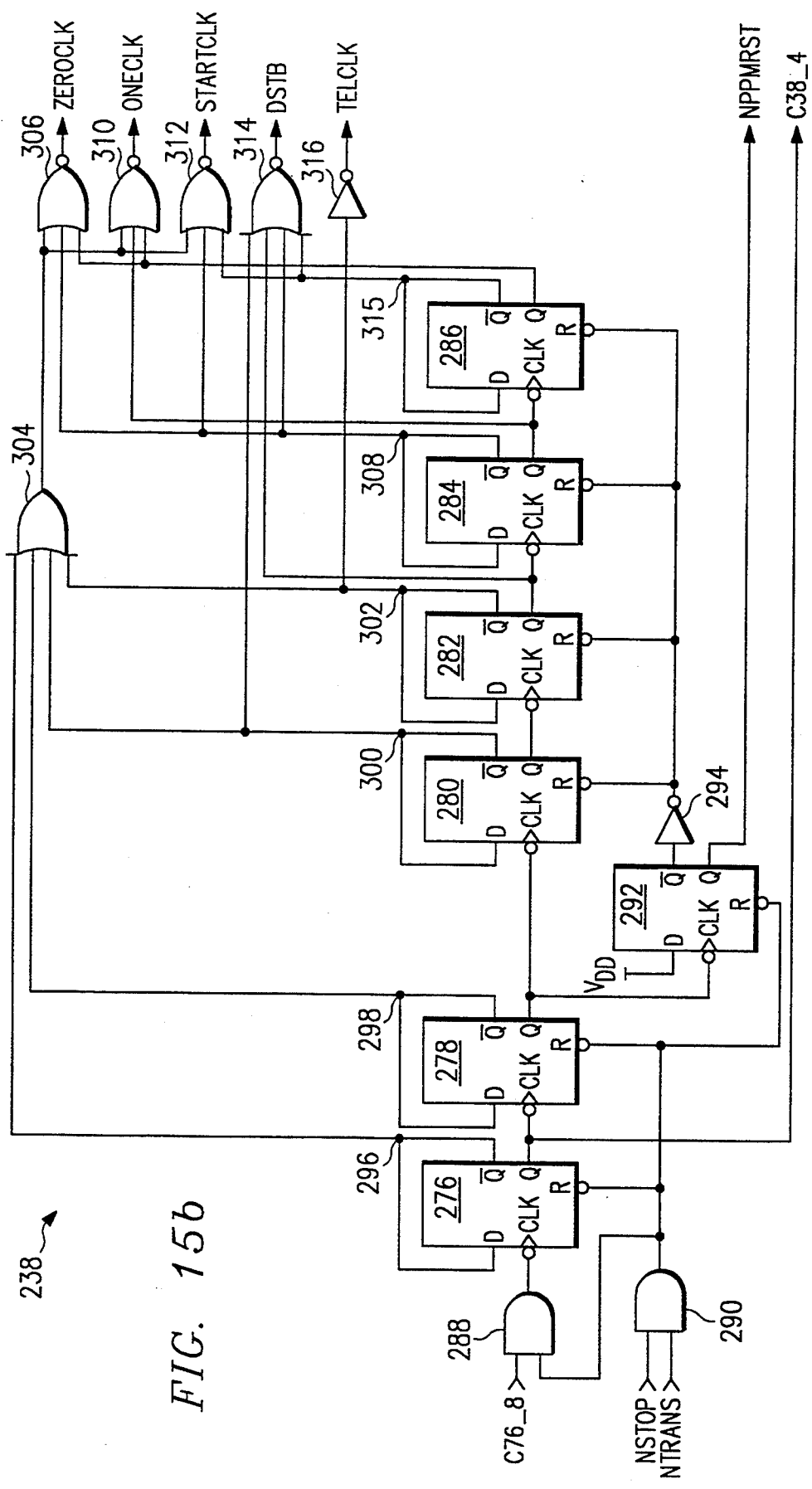

FIGS. 15a and 15b illustrate schematically the PPM decoder circuit 58 depicted in FIG. 8a. PPM decoder circuit 58 comprises; a PPM clock decode block 238 and related data checking logic. Block 238 as depicted in the FIGURE generates; C38_4, ZEROCLK, ONECLK, STARTCLK, DSTB and NPPMRST. Block 238 also generates signal TELCLK, a timing signal, for use within PPM decoder circuit 58. Block 238 is more fully described in connection with FIG. 15b.

FIG. 15a comprises five cascading D-type flipflops 240, 242, 244, 246 and 248. As depicted, the output of flipflops 240, 242, 244 and 246 are connected to the input of the next flipflop. Flipflop 240 is clocked by NREC_OUT inverted by an inverter 250. Flipflop 240 is reset by TELCLK after that signal is momentarily delayed by delay circuit 252. (Delay circuit 252 might be an AND gate with both of its inputs tied to TELCLK.) Flipflops 242, 244, 246 and 248 are each clocked by TELCLK and reset by NRST.

A NAND gate 254 ensures that the data bit input on NREC_OUT complies with the communication protocol described in FIG. 9a. Gate 254 has three inputs, the inverted output of flipflop 242, the output of an XOR gate 256 and the output of flipflop 248. The inputs to gate 256 are connected to the outputs of flipflops 244 and 246.

DATA is generated from the output of flipflop 246. REC_OFF is generated from the inverted output of a D-type flipflop 258 inverted by an inverter 260. Flipflop 258 has its input connected to $V_{DD}$ and is clocked by NTRANS. The reset signal to flipflop 258 is connected to the output of a RS flipflop 262. Flipflop 262 has a first input from the output of a NAND gate 264 and a second from the output of inverter 250. NAND gate 264 has inputs NRST and the output of a NAND gate 266. NAND gate 266 is a three input NAND gate having inputs of the inverted output of flipflop 258, DSTB and the output of a NAND gate 254. The set input to flipflop 242 is connected to the output of a NAND gate 268. The inputs to NAND gate 268 are connected to the output of inverter 250 and to NPPMRST through an inverter 270.

T-gates 272 and 274 alternately switch REC_OUT and TELCLK to TP4 under control of TEST. When TEST equals zero, TP4 is connected to the 4800 Hz signal TELCLK. When TEST equals one TP4 is connected to REC_OUT.

In operation, flipflops 240, 242, 244, 246 and 248 capture data present on NREC_OUT which is synchronized with the 4800 Hz TELCLK signal. Gate 254 ensures that the data bit follows the PPM protocol described in connection with FIG. 9a. Gate 254 outputs a high signal if any of the three PPM conditions are not met: (1) the start bit is high, (2) either the second or third bit is high, but not both or neither and (3) the no pulse detected window is low. Flipflop 258 and inverter 260 generate REC_OFF.

FIG. 15b illustrates a schematic diagram of PPM clock decode block 238 depicted in FIG. 15a. Block 238 comprises six D-type flipflops 276, 278, 280, 282, 284 and 286. These flipflops are cascaded together such that the output of flipflops 276, 278, 280, 282 and 284 are connected to the clock input of flipflops 278, 280, 282, 284 and 286, respectively. The clock input to flipflop 276 is connected to the output of AND gate 288. Gate 288 has two inputs, C76_8 and the output of an AND gate 290. AND gate 290 has inputs NSTOP and NTRANS. The output gate 290 is also connected to the resets of flipflops 276, 278 and to a D-type flipflop 292. Flipflop 292 is clocked by the output of flipflop 278 and its input is held high by $V_{DD}$. The output of flipflop 292 generates the signal NPPMRST. The inverted output of flipflop 292 inverted by an inverter 294 resets flipflops 280, 282, 284 and 286.

The input and inverted output of each of flipflops 276, 278, 280, and 282 are tied together to form nodes 296, 298, 300, and 302. These nodes form the inputs to OR gate 304. ZEROCLK is generated by a NOR gate 306. Gate 306 has three inputs, the output of gate 304, a node 308 and the output of flipflop 286. Node 308 is connected to the input and inverted output of flipflop 284. ONECLK is generated by a NOR gate 310. Gate 310 has three inputs, the output of gate 304, the output of flipflop 284 and the output of latch 286. STARTCLK is generated by a NOR gate 312. NOR gate 312 has three inputs, the output of gate 304, node 308 and the inverted output of flipflop 286. DSTB is generated by a NOR gate 314. NOR gate 314 has four inputs, node 300, the output of flipflop 282, node 308 and a node 315. Node 315 is connected to the input and the inverted output of flipflop 286. TELCLK is generated from node 302 inverted by an inverter 316.

g. Communications Modem

Figure 16:
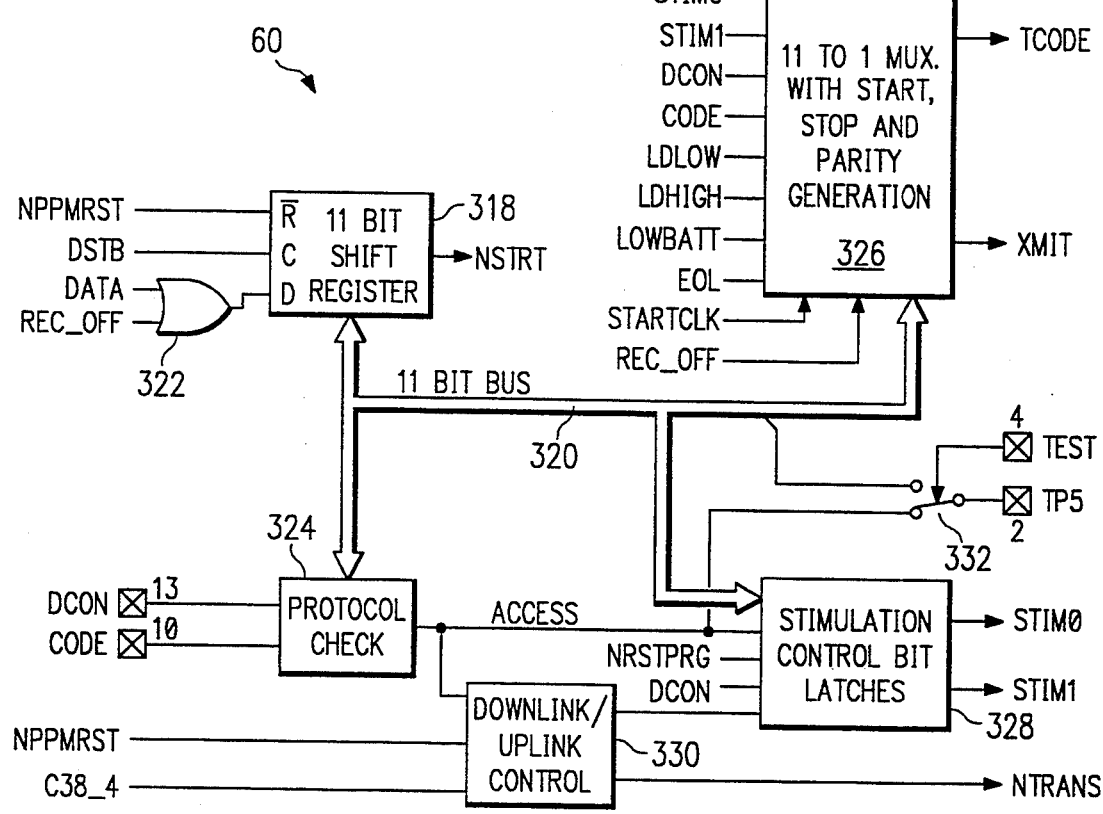
FIG. 16 illustrates a block diagram of the communication modem circuit depicted in FIG. 8b.

FIG. 16 illustrates a block diagram of the communication modem circuit 60 depicted in FIG. 8b. Communication modem circuit 60 comprises an 11 bit shift register 318 with outputs NSTRT and an 11 bit bus 320. Shift register 318 is reset by NPPMRST and is clocked by DSTB. DATA and REC_OFF are logically combined by an OR gate 322. The output of gate 322 is the data input to shift register 318. Bus 320 connects shift register 318 to protocol check circuit 324, to 11-to-1 multiplexer 326 and to stimulation control bit latches 328.

Protocol check circuit 324 has inputs DCON, CODE through pads 13 and 10, respectively. Protocol check circuit 324 has a single output ACCESS input to latches 328 and to a downlink/uplink control circuit 330. Latches 328 also have inputs NRSTPRG, DCON, and the output from circuit 330. Latches 328 output STIM0 and STIM1. Circuit 330 also has inputs NPPMRST and C38_4. As depicted, multiplexer 326 has data inputs STIM0, STIM1, DCON, CODE, LDLOW, LDHIGH, LOWBATT, and EOL. Multiplexer 326 also has two control inputs STARTCLK and REC_OFF. Multiplexer 326 outputs TCODE and XMIT.

A switch 332 alternately switches an external connection, TP5, to either the tenth data line in bus 320 or to ACCESS depending upon the logic value of TEST. If TEST=0, then TP5 is connected to ACCESS. If TEST=1, TP5 is connected to a data line within bus 320 containing the final or stop bit of information. Pad 2 is connected to TP5 while pad 4 is connected to TEST.

In operation, 11 bits of data are strobed into shift register 318 through DSTB and DATA. These bits are then made available on bus 320. Protocol check circuit 324 then compares the received data with the programmed data word requirements described in connection with FIG. 9b. If these requirements are met, then protocol check circuit 324 outputs a logic one on ACCESS. Latches 328 check the second received data bit to determine if STIM0 and STIM1 should be written to (RNW=0) or simply read from (RNW=1). If a write command is indicated on bus 320, latches 328 will be loaded with new data. If only a read operation is indicated, communication modem 60 will uplink a handshake communication to the external receiver. Circuit 330 outputs a logic zero on NTRANS after a valid communication is received as indicated by protocol check circuit 324.

After a valid downlink, communication modem 60 outputs 11 data bits according to the communication protocol described in connection with FIG. 9c on TCODE. Multiplexer enables transmitter circuit 56 through XMIT. Multiplexer 326 outputs each bit in the proper order by receiving sequentially a jammed bit on each of the 11 bus lines 320 from shift register 318. A logic 1 is jammed into shift register 318 through REC_OFF. Multiplexer 326 sequentially enables each data line as the one ripples through bus 320. This procedure causes the contents of STIM0, STIM1 DCON CODE LDLOW LDHIGH, LOW, BATT and EOL data lines along with the start bit to be serially outputted through TCODE in the proper order without requiring an address counter. An internal toggle generates an odd parity bit after the last data bit is output and immediately prior to the stop bit. It should be understood that a conventional multiplexer with address bits could be employed in place of multiplexer 326.

h. Lead Status

Figure 17:
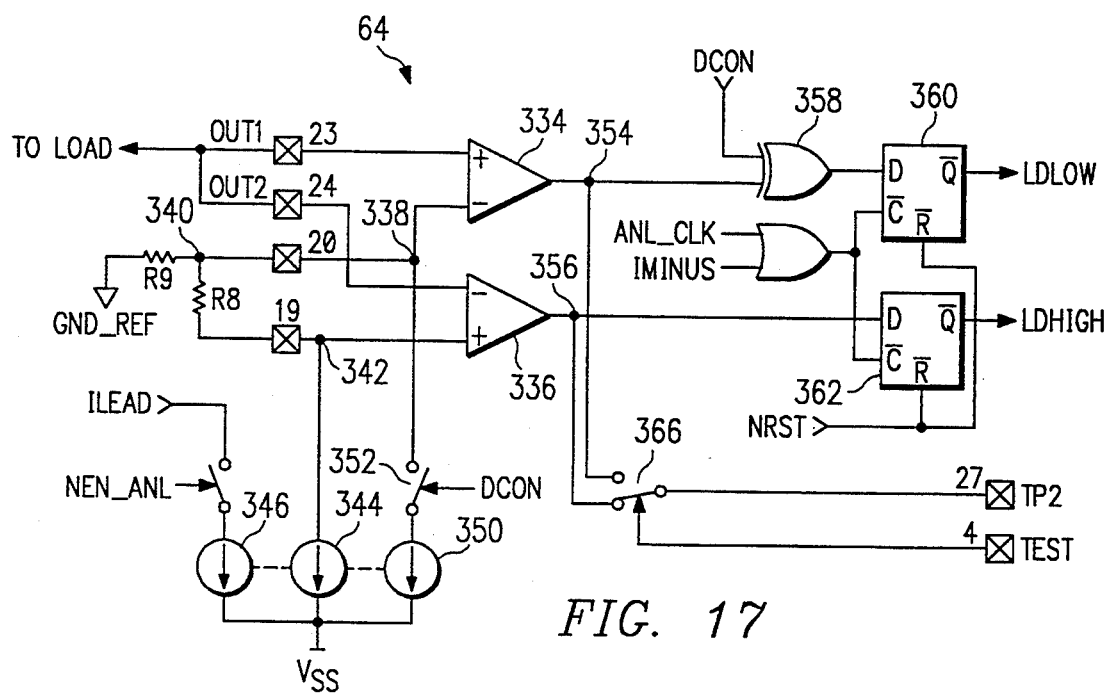
FIG. 17 illustrates schematically the lead status circuit depicted in FIG. 8b.

FIG. 17 illustrates schematically the lead status circuit 62 depicted in FIG. 8b. Lead status circuit 62 comprises a first and second comparator 334 and 336. OUT1 is connected to the first input of comparator 334 through pad 23. A node 338 is connected to the second input of comparator 334. Node 338 is also connected to node 340 through external pad 20. Node 340 is connected to GND_REF through resistor R9. The first input to comparator 336 is connected to node 342. Node 342 is connected to a node 340 through external resistor R8 and pad 19. Node 342 is also coupled to a current mirror 344. Current mirror 344 is connected to $V_{SS}$ and mirrors current through a current mirror 346. Current mirror 346 is connected to ILEAD through switch 348 under the control of NEN_ANL current mirror. Current mirror 346 is also connected to $V_{SS}$. Node 338 is coupled to a second current mirror 350 through a switch 352 under the control of DCON. Current mirror 350 also mirrors current mirror 346 and is connected to $V_{SS}$. The outputs to comparators 334 and 336 are connected to nodes 354 and 356. Node 354 is one input to a XOR gate 358. Gate 358 has DCON as its second input. The output to gate 358 is connected to the input of a flipflop 360. Node 356 is connected to the input of a flipflop 362. Flipflops 360 and 362 are reset by NRST and are clocked by the output from an OR gate 364. Gate 364 has inputs ANL_CLK and IMINUS. Flipflops 360 and 362 generate LDLOW and LDHIGH, respectively.

Switch 366 alternately connects TP2 through pad 27 to each of the outputs of comparators 334 and 336. Switch 366 is under the control of TEST through pad 4. When TEST equals 0, TP2 is connected to node 356. When TEST equals 1, TP2 is connected to node 354.

In the AC mode of operation, the bone growth stimulator has a single electrode output. OUT1 and OUT2 are therefore shorted together off chip. Comparator 334 compares the voltage on OUT1 to the voltage at node 340. If voltage on OUT1 drops below the voltage at node 340, comparator 334 will output a zero to latch 360 and onto LDLOW. The voltage at node 340 is determined by the choice of resistor R9. Comparator 336 compares the voltage on OUT1 with a voltage at node 342. When the voltage on OUT2 exceeds the voltage at node 342, comparator 336 outputs a logic level zero which is latched by flipflop 362 and output on LDHIGH. The voltage at node 342 is determined by the choice of resistors R8 and R9. NEN_ANL disables lead status circuit 62 during the positive portion and rest portion of the output signal to conserve power. Current mirror 344 sinks nA 100 of current from node 342.

In the DC mode of operation, OUT1 and OUT2 are each connected to a cathode through pads 23 and 24. Also, node 342 is connected to GND_REF through resistor R8. (Resistor R8 is not connected to node 340). Switch 352 is closed by DCON, allowing current mirror 350 to sink nA 100 from node 338. Both comparators 334 and 336 compare the voltages on OUT1 and OUT2 to the voltages on nodes 338 and 342, respectively. Comparator 334 will output a logic level zero if OUT1 is lower than the voltage at node 340 (high lead impedance on OUT1). Comparator 336 will output a logic level one if OUT2 is lower than the voltage at made 342 (high lead impedance on OUT2). These outputs will be latched by flipflops 360 and 362.

i. Receiver

FIG. 18 illustrates schematically the receiver circuit 64 depicted in FIG. 8a. Receiver circuit 64 comprises a power transconductance comparator 368 which outputs NREC_OUT. The first input to comparator 368 is connected to a node 370. The second input is connected to an internal voltage supply which will range from 75 to 150 mV. Current is sunk from node 370 by a current source 372. Current source 372 is coupled to $V_{SS}$. Node 370 is connected to an external node 220 by resistor R3 through external pad 9. Node 370 is also connected to $V_{DD}$ through inductor L1. Pad 8 is an external connection for a transmitter circuit 56. It is connected to node 374 through capacitor C2.

As described inn connection with FIG. 14, inductor L1 has an inductance of 4.8 mH, resistor R3 has a resistance of 10 kOhms and capacitor C2 has a capacitance of 1000 pF.

In operation, comparator 368 pulses low when inductor L1 receives a pulse from an external transmitter. Comparator 368 can detect a pulse of approximately 20 mV in amplitude, 7.5 μsec in width, and pulses spaced as close together as 75 μsec.

j. Battery Status Indicator

FIG. 19 illustrates schematically the battery status indicator circuit 66 depicted in FIG. 8b. Battery status circuit 66 comprises a comparator 376. The output from comparator 376 is logically combined with REC_OFF by an AND gate 378. The output of gate 378 is connected to the input of a latch 380. Latch 380 is reset by NRST and its output generates LOWBATT. The output of latch 380 is combined with the output from gate 378 by an AND gate 382. The output of AND gate 382 is connected to the input of a latch 384. Latch 384 is reset by NRST and clocked by C1_49. Latch 384 requires two clock cycles to latch. The output of latch 384 generates EOL.

The first input to comparator 376 is connected to a node 386. Node 386 is connected to an external node 388 through EOLTRM and pad 12. External capacitor C3 is connected between node 388 and $V_{DD}$. An external resistor R4 is connected between the node 388 and $V_{SS}$. Two current mirrors 390 and 392 are connected in parallel between node 386 and a node 394. A switch 396 selectively connects current source 392 to node 394 under control of the output of latch 380. Node 394 is coupled to $V_{DD}$ by a switch 398 under control of NEN_ANL. The second input of comparator 376 is connected to GND_REF.

A switch 400 alternately connects TP3 through pad 28 to either the output of gate 378 or the output of latch 384. Switch 400 is controlled by TEST through external pad 4. When TEST equals zero, TP3 is connected to the output of gate 378. When TEST equals one, TP3 is connected to the output of latch 384.

In operation, comparator 376 compares the voltage at node 386 with GND_REF. The first voltage, that of node 386, is constant depending upon how much current is drawn through resistor R4 by current mirrors 390 and 392. GND_REF however drops as $V_{DD}$ drops during the lifetime of the circuit.

Initially, the output of latch 380 is low and switch 396 is closed. Current mirrors 390 and 392 sink 120 nA through resistor R4. Initially, GND_REF is at a higher potential than node 386. The output of comparator 376 is therefore low. As the battery ages, GND_REF will drop below the constant voltage at node 386 and trip the output of comparator 376 high. This will output a LOWBATT bit from latch 380 and open switch 396. Node 386 will therefore only have 80 nA current flowing through it. This will lower the voltage of node 388. GND_REF will again be higher than the voltage at node 386 causing output of comparator 376 to go low again. Eventually as the battery continues to age, GND_REF will drop below the second, even lower, voltage level at node 386 tripping the output of comparator 376 high. The second high output will be combined with the output from latch 380 by gate 382 and output as EOL.

k. Voltage Reference/Regulator

FIG. 20 illustrates a block diagram of the voltage reference/regulator circuit 68 depicted in FIG. 8b. Voltage reference/regulator circuit 68 comprises a diode 403 connected to $V_{DD}$ and node 402, biased as depicted. Node 402 is connected to $V_{SS}$ through a current mirror 404. A second diode 405 is connected between $V_{DD}$ and VSET1 through pad 15. VSET1 is coupled to VSET2 through external resistor R5. VSET2 exits the circuit through pad 16. VSET2 is coupled to a node 406. Node 406 is coupled to $V_{SS}$ through a current mirror 408. An op-amp 410 has its first input to node 406 and its second input connected to node 402. An external resistor R6 is connected between $V_{DD}$ and pad 16. External resistor R7 is connected between $V_{DD}$ and a node 412. Node 412 is coupled to VREF through pad. 17. Pad 17 is connected to $V_{SS}$ through a current mirror 414. Node 412 is the first input of comparator 416. The second input to comparator 416 is tied to its output. The output of comparator 416 generates GND_REF (internally and GND_externally). GND_REF is coupled to one terminal of an external capacitor C5 through external pad 18. The second terminal of capacitor C5 is coupled to $V_{DD}$. First and second current mirrors 418 and 420 are connected in series between $V_{DD}$ and $V_{SS}$. Current mirrors 422 and 424 are coupled to $V_{DD}$ and generate the 20 nA bias currents IREC_and ILEAD respectively. ITEST is connected to $V_{SS}$ through a current mirror 426. IDCON is connected to $V_{SS}$ through a current mirror 428. ICODE is connected to $V_{SS}$ through a current mirror 430. IBATT is connected to $V_{SS}$ through a current mirror 432. IPOR is connected to $V_{SS}$ through a current mirror 434. Current mirrors 426, 428, and 430 generate 100 nA bias currents. Current mirrors 432 and 434 generate a 20 and 10 nA bias current respectively.

NRSTPRG controls a switch 436. Switch 436 connects $V_{DD}$ to a current mirror 438. The output of voltage mirror 438 is connected to output of comparator 410. The currents flowing through current mirrors 438, 404, 408, 414, 420, 426, 428, 430, 432 and 434 governed by the output of comparator 410 and are compensated for variation in temperature as will be described below. Current mirrors 4181, 422 and 424 are controlled by the output of comparator 410 through current mirror 420. Current mirror 438 enables voltage reference/regulator circuit 68.

Voltage reference/regulator circuit 68 is based on the Band Gap principal. Comparator 410 sets the current mirrors such that the voltages at nodes 402 and 406 are equal. Therefore, the current through R6 is directly proportional to the single diode 403. The current through R5 is based on the difference in the two diodes 403 and 405, which are selected to have an 8:1 difference in current density. When R5 is selected in the proper balance with R6 (R6/R5=16.2), the current sum will be temperature independent. VREF is set by the mirrored current and external resistor R7. In the illustrated embodiment, VREF equals GND (GND_REF) or $V_{DD}-1.5$ Volts.

5. Stimulator Circuit Configurations a. AC Configuration

Figure 21:
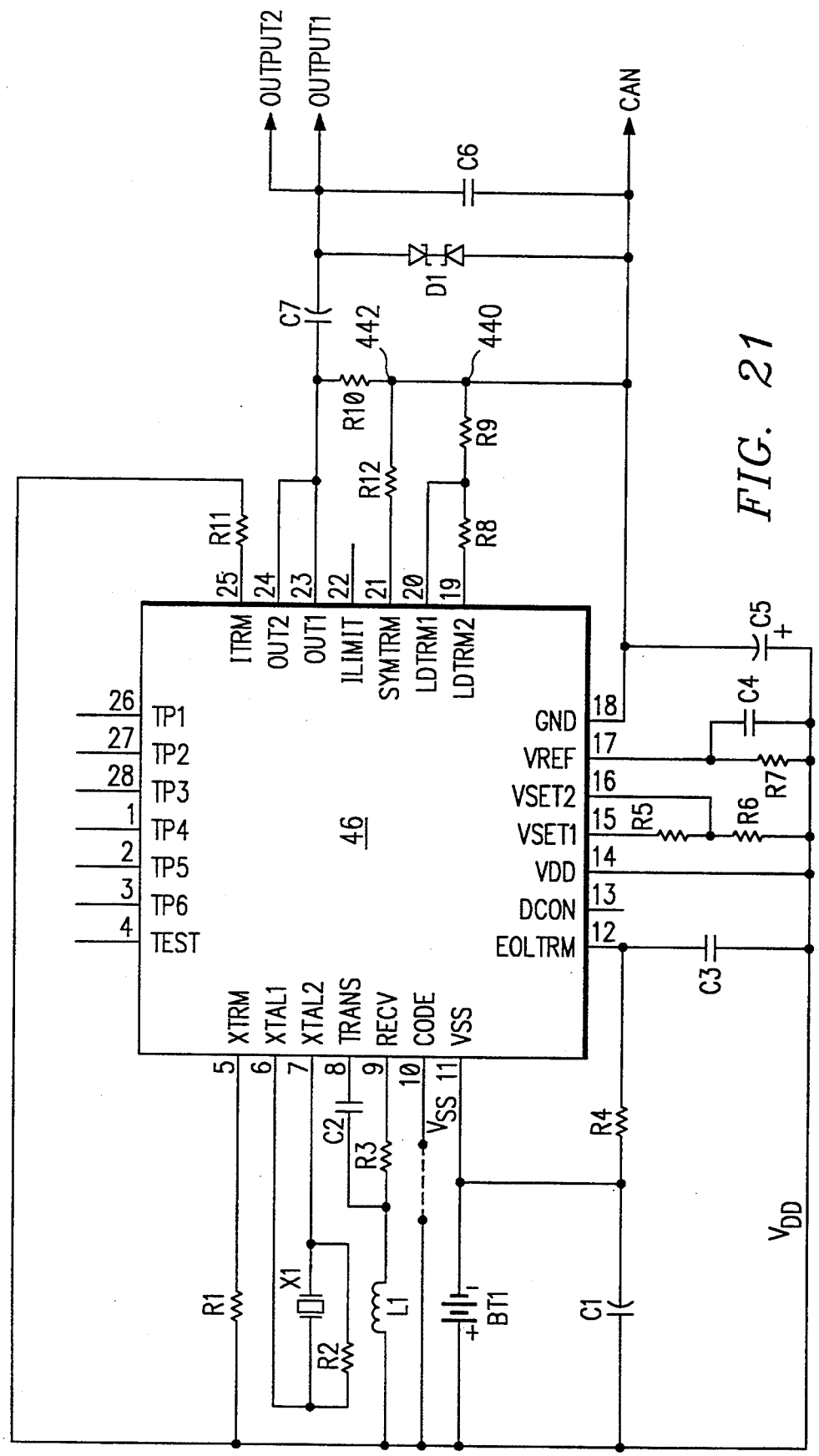
FIG. 21 illustrates schematically the circuit depicted in FIGS. 8a and 8b configured for the AC mode of operation.

FIG. 21 illustrates schematically the circuit depicted in FIGS. 82 and 85 configured for the AC output signal. When packaged, pins 1-4 and 26-28 are left open on integrated circuit 46. Testing is done before final assembly.

XTRM is connected to $V_{DD}$ 5 through resistor R1. Resistor R1 is a 10 MOhm resistor. XTAL1 is connected to crystal X1 in parallel with resistor R2. XTAL2 is connected to the other terminal of crystal X1 and resistor R2. Crystal X1 is a 76.8 kHz crystal and resistor R2 has a resistance of 20 MOhm. TRANS, is connected to one terminal of capacitor C2. RECV is connected to the first terminal of external resistor R3. The remaining terminal of capacitor C2 and resistor R3 are tied together and to the first terminal of inductor L1. The second terminal of inductor L1 is connected to $V_{DD}$. Capacitor C2 has a capacitance of 1,000 pF, resistor R3 has a resistance of 10 kOhm, and inductor L1 has an inductance of 4.8 mH. CODE may or may not be connected to $V_{DD}$ through external pad 10. $V_{SS}$ is connected to the negative terminal of battery BT1. Battery BT1 is a 2.8 volt lithium iodine battery rated for 200 mAH. A slightly larger battery may be substituted increasing the rating of the battery BT1 to 0.5 AH.

As depicted, $V_{SS}$ is also connected to one terminal of capacitor C1 and one terminal of resistor R4. The second terminal of capacitor C1 is connected to $V_{DD}$ and the second terminal of resistor R4 is connected to EOLTRIM. EOLTRIM is also connected to $V_{DD}$ through capacitor C3. Capacitors C1 and C3 have a capacitance of 22 µF and 100 pF respectively. Resistor R4 is actively trimmed with a range of 3-9 MOhm to achieve a LOWBATT trippoint of 2.4 prior to final assembly. DCON is left floating at external pad 13. $V_{DD}$ is connected to the positive terminal of battery BT1. VSET1 is connected to $V_{DD}$ through resistor series combination of resistors R5 and R6. VSET2 is connected to the node formed by the inner connection of resistor R5 to resistor R6. VREF is connected to parallel resistor/capacitor combination. Parallel resistor capacitor combination comprises resistor R7 and capacitor C4. The second terminal of R7 and C4 are connected to $V_{DD}$. Resistors R6 and R7 have a resistance of 18.75 MOhm. Resistor R5 is actively trimmed prior to assembly to generate GND=$V_{DD}-1.5$ Volts. GND_is coupled to $V_{DD}$ through capacitor C5 and to the electrode window on the bone growth stimulator.

LDTRM2 is connected to a node 440 through a resistor series comprising resistors R8 and R9. Node 440 is connected to GND. LDTRM1 is connected to the node formed by the connection of resistors R8 and R9. The low lead impedance trippoint is set by actively trimming resistor R9. The high impedance trippoint is set by actively trimming resistor R8 after resistor R9. SYMTRIM is connected to a node 442 through optional resistor R12. SYMTRIM exits integrated circuit 46 at external pad 22. OUT1 is connected to the output electrode through capacitor C7. Capacitor C7 ensures that the output has no net DC component. Capacitor C7 has the capacitance of 10 µF. OUT1 is also connected to node 442 through resistor R10. Resistor R10 has a resistance of 2 MOhm. Nodes 442 and 440 are electrically connected. OUT2 is connected to OUT1. ITRIM is connected to $V_{DD}$ through resistor R11. Resistor R11 is actively trimmed to set the output current. In addition, zener diode D1 is coupled between GND_and output and are biased as depicted. They provide high voltage protection to the circuit. Capacitor C6 is also connected between OUTPUT1 and GND_. Capacitor C6 protects the circuit from EMI. Capacitor C6 has a capacitance of 1,000 pF.

b. DC Configuration

Figure 22:
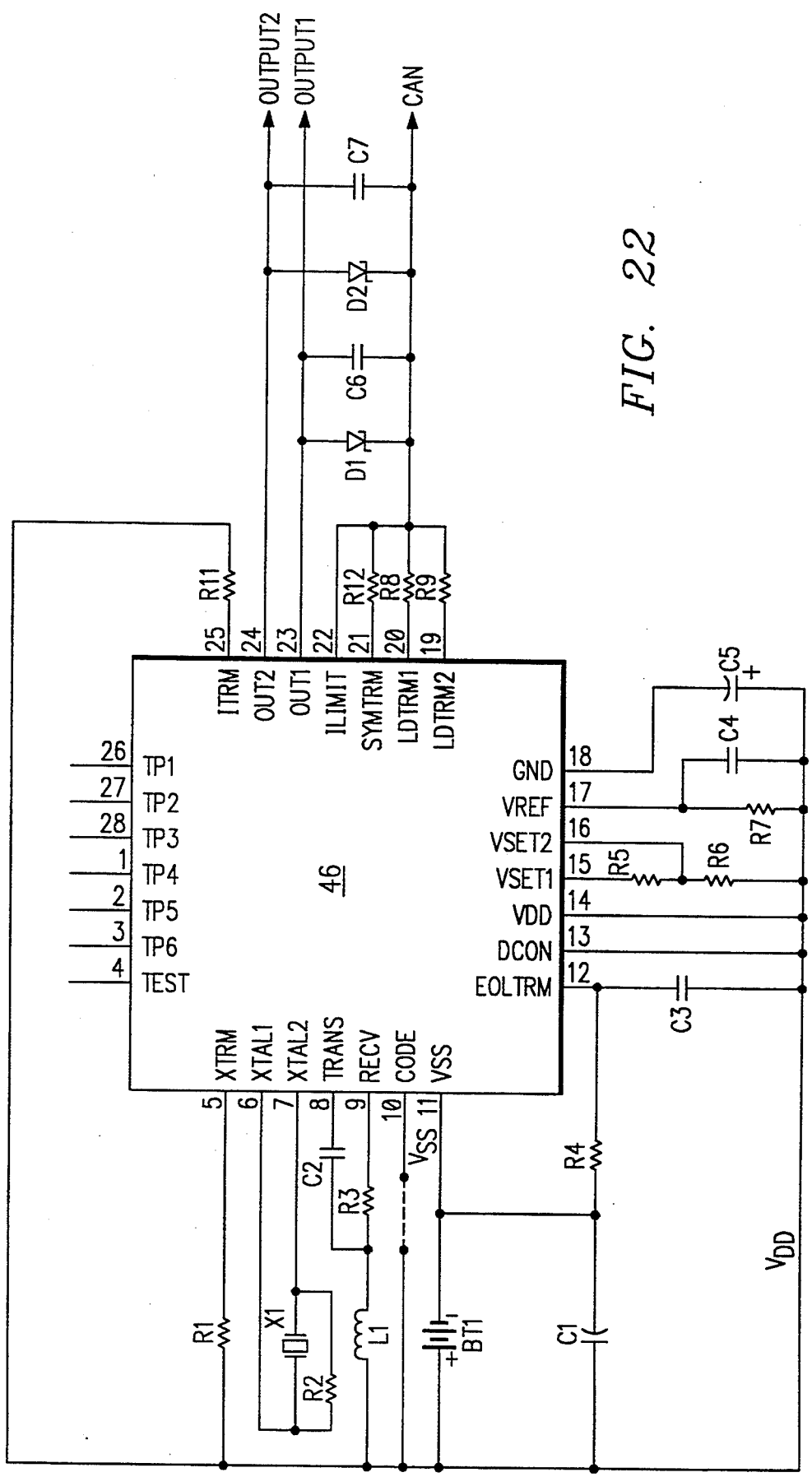
FIG. 22 illustrates schematically the circuit depicted in FIGS. 8a and 8b configured for the DC mode of operation.

FIG. 22 illustrates schematically the circuit depicted in FIGS. 8a and 8b configured for the DC output signal. Integrated circuit 46 has substantially the same configuration for the DC output as for the AC output. There are the following differences: DCON is connected to $V_{DD}$ to indicate the DC mode of operation. OUT2 is connected to the second cathode. Each output has a parallel zener diode/capacitor combination between it and LDTRM1. Diode D1 and capacitor C6 are connected in parallel between OUT1 and ILIMIT. Diode D2 and capacitor C7 are connected in parallel between OUT1 and ILIMIT. ILIMIT is connected to the anode, CAN.

Certain resistors and capacitors may have different values to reflect the DC configuration. This adjustment can be made by one skilled in art in connection with the foregoing description.

Although the present invention and its advantages have been described in detail, it should be understood that various changes, substitutions and alterations can be made herein without departing from the spirit and scope of the invention as defined by the appended claims.

What is claimed is:

1. An implantable growth stimulator having a status, the stimulator comprising:

first and second plate electrodes for subcutaneous implantation at a predetermined distance from a tissue site;

a thin elongate member of elastomer connecting and generally maintaining a predetermined distance between said first and second electrodes;

a portion of each electrode being exposed to allow current flow therethrough; and a driver circuit having means for generating for a duration of time, an alternating current between said first and second electrodes thereby producing first and second monitorable voltages on said first and second electrodes, respectively, said alternating current operative to stimulate tissue growth at the tissue site.

2. The stimulator of claim 1 wherein said driver circuit further comprises a switch circuit having means for generating an asymmetric alternating current.

3. The stimulator of claim 1 wherein said driver circuit further comprises a switch circuit having means for generating a symmetric alternating current.

4. The stimulator of claim 1 further comprising:

a receiver circuit having means for receiving signals transmitted external to the stimulator, the signals representative of a desired mode of operation of the stimulator; and a time base circuit having means for modifying the mode of operation of the stimulator responsive to the transmitted signals.

5. The stimulator of claim 4 wherein said time base circuit further comprises a divide-by circuit having means for modifying the duration of time the stimulator generates the alternating current.

6. The stimulator of claim 1 further comprising:
a modem circuit having means for monitoring the status of the stimulator and for generating signals representative of the status of the stimulator; and
a transmitter circuit having means for transmitting the signals to a receiver external to the stimulator.

7. The stimulator of claim 6 further including a battery wherein said modem circuit comprises a battery status circuit having means for monitoring a voltage drop across said battery within the stimulator.

8. The stimulator of claim 6 wherein said modem circuit further comprises a lead status circuit having means for monitoring one of the voltages.

9. The stimulator of claim 6 wherein said modem circuit monitors the duration that said driver circuit outputs the alternating current.

10. The stimulator of claim 1 wherein said thin elongate member further comprises silicon.

11. The stimulator of claim 1 wherein said thin elongate member further comprises urethane.

12. The stimulator of claim 1 wherein said thin elongate member further comprises silicon-urethane.

13. An implantable growth stimulator comprising:
first and second electrodes spaced apart a predetermined distance for being subcutaneously implanted a predetermined distance from a tissue site;
a thin elongate member of elastomer for connecting and generally maintaining predetermined distance between said first and second electrodes;
a driver circuit connected to said first and second electrodes having means for generating, for a duration of time, an alternating current between said first and second electrodes in order to stimulate tissue growth;
a receiver circuit connected to said driver circuit having means for receiving external signals, the external signals representative of a desired mode of operation of the stimulator;
a time base circuit connected to said driver circuit having means for modifying the mode of operation of the stimulator responsive to the external signals; and
a modem circuit connected to said driver circuit having means for generating signals representative of a status of the stimulator; and
a transmitter circuit connected to said modem circuit having means for transmitting the signals to an external receiver.

14. The stimulator of claim 13 further including a battery wherein said modem circuit comprises a battery status circuit having means for monitoring a voltage drop across said battery within the stimulator.

15. The stimulator of claim 13 wherein said modem circuit further comprises a lead status circuit having means for monitoring a voltage on one of said first and second electrodes.

16. The stimulator of claim 13 wherein said modem circuit monitors the duration of time said driver circuit outputs the alternating current.

17. The stimulator of claim 16 further comprising a divider circuit and wherein the duration of time is controlled by a said divider circuit to be zero, four, eight or twenty-four hours per day.

18. The stimulator of claim 13 wherein said thin elongate member further comprises silicon.

19. The stimulator of claim 13 wherein said thin elongate member further comprises urethane.

20. The stimulator of claim 13 wherein said thin elongate member further comprises silicon-urethane.

21. An implantable growth stimulator comprising:
first and second plate electrodes for being subcutaneously implanted adjacent a tissue site;
a portion of each electrode being exposed to allow current flow therethrough;
a driver circuit connected to said electrodes having a switch circuit having means for generating an alternating current between said first and second electrodes, said alternating current operative to generate an electric field having a negative excursion at the tissue site between $-0.3$ and $-3$ mV/cm so as to promote healing at the tissue site.

22. A method for the therapeutic stimulation of a tissue site comprising the steps of:
subcutaneously implanting a growth stimulator into a tissue near the tissue site, the stimulator having first and second electrodes disposed a predetermined distance from the tissue site; and
generating an alternating current flowing through an exposed portion of the first and second electrodes operative to generate an electric field having a negative excursion at the tissue site between $-0.3$ and $-3$ mV/cm so as to promote healing at the tissue site.

* * * * *

UNITED STATES PATENT AND TRADEMARK OFFICE
CERTIFICATE OF CORRECTION

PATENT NO. : 5,441,527

DATED : August 15, 1995

INVENTOR(S) : Erickson, et al.

It is certified that error appears in the above-identified patent and that said Letters Patent is hereby corrected as shown below:

Column 3, line 27, delete "inventions" and insert -- invention --;

Column 3, line 46, after "growth", delete ":".

Column 9, line 58, after "externally", delete "hardwired", and insert -- hard-wired --.

Column 11, line 60, delete "NEN ANL_" and insert -- NEN_ANL --.

Column 15, line 40, after "132." delete "NEN ANL_" and insert -- NEN_ANL --.

Column 17, line 56, after "comprises", delete ";";

Column 17, line 58, after "generates", delete ";".

Column 20, line 2, after STIM1" insert -- , --;

Column 20, line 2, after "DCON", insert -- , --;

Column 20, line 2, after "CODE", insert -- , --;

Column 20, line 3, after "LDLOW", insert -- , --.

UNITED STATES PATENT AND TRADEMARK OFFICE
CERTIFICATE OF CORRECTION

PATENT NO. : 5,441,527

DATED : August 15, 1995

INVENTOR(S) : Erickson, et al.

It is certified that error appears in the above-identified patent and that said Letters Patent is hereby corrected as shown below:

Column 21, line 23, after "described," delete "inn", and insert -- in --.

Column 22, line 37, after "pad", delete ".".

Column 22, line 41, after "GND", delete "_";

Column 22, line 48, after "IREC", delete "_".

Column 22, line 64, after "mirrors", delete "4181", and insert -- 418 --.

Column 23, line 60, after "GND", delete "_".

Column 24, line 13, after "GND", delete "_";

Column 24, line 16, after "GND", delete "_".

Column 25, line 13, after "monitoring" delete "the", and insert -- a --;

Column 25, line 40, after "elastomer", delete "for".

UNITED STATES PATENT AND TRADEMARK OFFICE
CERTIFICATE OF CORRECTION

PATENT NO. : 5,441,527
DATED : August 15, 1995
INVENTOR(S) : Erickson, et al.

It is certified that error appears in the above-indentified patent and that said Letters Patent is hereby corrected as shown below:

Column 26, line 22, after "by", delete "a".

Signed and Sealed this

Eighth Day of July, 1997

Attest:

BRUCE LEHMAN

Attesting Officer

Commissioner of Patents and Trademarks